(12) United States Patent
Takagi et al.

(10) Patent No.: US 10,550,364 B2
(45) Date of Patent: Feb. 4, 2020

(54) METHOD FOR PRODUCING WNT PROTEIN AND METHOD FOR STORING WNT PROTEIN

(71) Applicant: OSAKA UNIVERSITY, Osaka (JP)

(72) Inventors: Junichi Takagi, Osaka (JP); Emiko Mihara, Osaka (JP); Akira Kikuchi, Osaka (JP)

(73) Assignee: OSAKA UNIVERSITY, Osaka (JP)

( * ) Notice: Subject to any disclaimer, the term of this patent is extended or adjusted under 35 U.S.C. 154(b) by 165 days.

(21) Appl. No.: 15/539,241

(22) PCT Filed: Dec. 24, 2015

(86) PCT No.: PCT/JP2015/086102
§ 371 (c)(1),
(2) Date: Jun. 23, 2017

(87) PCT Pub. No.: WO2016/104646
PCT Pub. Date: Jun. 30, 2016

(65) Prior Publication Data
US 2017/0355953 A1    Dec. 14, 2017

(30) Foreign Application Priority Data

Dec. 24, 2014  (JP) ................................. 2014-260792

(51) Int. Cl.
| | | |
|---|---|---|
| C12N 5/00 | (2006.01) | |
| A61K 38/00 | (2006.01) | |
| C07K 19/00 | (2006.01) | |
| C12P 21/02 | (2006.01) | |
| C12N 15/09 | (2006.01) | |
| C07K 14/00 | (2006.01) | |

(52) U.S. Cl.
CPC ............ *C12N 5/0018* (2013.01); *A61K 38/00* (2013.01); *C07K 19/00* (2013.01); *C12N 15/09* (2013.01); *C12P 21/02* (2013.01); *C07K 14/00* (2013.01); *C12N 2501/415* (2013.01)

(58) Field of Classification Search
None
See application file for complete search history.

(56) References Cited

U.S. PATENT DOCUMENTS

| | | | |
|---|---|---|---|
| 5,652,352 A | 7/1997 | Lichenstein et al. | |
| 5,767,243 A | 6/1998 | Lichenstein et al. | |
| 2014/0200179 A1 | 7/2014 | Garcia et al. | |
| 2015/0099708 A1 | 4/2015 | Lee et al. | |

FOREIGN PATENT DOCUMENTS

| | | |
|---|---|---|
| JP | 9-511399 | 11/1997 |
| JP | 2006-345702 | 12/2006 |
| JP | 2014-506568 | 3/2014 |
| JP | 2014-527818 | 10/2014 |

OTHER PUBLICATIONS

Kronenberg et al., "Plasma Concentrations of Afamin Are Associated With the Prevalence and Development of Metabolic Syndrome",Circulation. Cardiovascular Genetics, vol. 7, pp. 822-829 (Year: 2014).*
International Preliminary Report on Patentability dated Aug. 8, 2016 in International Application No. PCT/JP2015/086102.
International Search Report dated Feb. 23, 2016 in International Application No. PCT/JP2015/086102.
Roland Baron et al., "WNT signaling in bone homeostasis and disease: from human mutations to treatments", Nature Medicine vol. 19, No.2, Feb. 2013, pp. 179-192.
Jamie N. Anastas et al., "WNT signalling pathways as therapeutic targets in cancer", Nature Reviews Cancer, vol. 13, pp. 11-26, Jan. 2013.
J. K. Van Camp et al., "Wnt Signaling and the Control of Human Stem Cell Fate", Stem Cell Rev and Rep (2014),10, pp. 207-229.
Karl Willert et al., "Wnt proteins are lipid-modified and can act as stem cell growth factors", Nature, vol. 423, pp. 448-452, May 22, 2003.
Shosei Kishida et al., "Wnt-3a and Dvl Induce Neurite Retraction by Activating Rho-Associated Kinase", Molecular and Cellular Biology, vol. 24, No. 10, May 2004, pp. 4487-4501.
Claudia Y. Janda et al., "Structural Basis of Wnt Recognition by Frizzled", Science, vol. 337, pp. 59-64, Jul. 6, 2012.
Karl H. Willert, "Isolation and Application of Bioactive Wnt Proteins", vol. I, Pathway Methods and Mammalian Models, vol. 468, pp. 17-29, 2008.
Extended European Search Report dated May 29, 2018 in corresponding European patent application No. 15873214.9.
Lidija Jerkovic et al., "Afamin is a novel human vitamin E-binding glycoprotein characterization and in vitro expression", Journal of Proteome Research, American Chemical Society, vol. 4, No. 3, May 1, 2005, pp. 889-899.
Emiko Mihara et al., "Active and water-soluble form of lipidated Wnt protein is maintained by a serum glycoprotein afaim/[alpha]-albumin", Elife, vol. 5, Feb. 23, 2016.
Extended European Search Report dated Nov. 11, 2019 in European Application No. 19183227.8.

(Continued)

*Primary Examiner* — Michelle F. Paguio Frising
(74) *Attorney, Agent, or Firm* — Wenderoth, Lind & Ponack, L.L.P.

(57) ABSTRACT

Provided is a novel method for producing a Wnt protein, which method comprises (1) a step of performing affinity purification targeting afamin to obtain a Wnt protein from a culture product, and/or (2) a step of performing affinity purification to obtain a Wnt protein in the form of a complex with afamin from a culture product.

The method enables a Wnt protein having high Wnt activity to be produced in a simple and brief manner without use of special equipment.

15 Claims, 13 Drawing Sheets

Specification includes a Sequence Listing.

(56) References Cited

OTHER PUBLICATIONS

Sayumi Shibamoto et al., "Cytoskeletal reorganization by soluble Wnt-3a protein signaling", Genes to Cells, vol. 3, No. 10, 1998, pp. 659-670.

Girija R. Dhamdhere et al., "Drugging a Stem Cell Compartment Using Wnt3a Protein as a Therapeutic", PLOS ONE, vol. 9, No. 1, 2014, 11 pages.

* cited by examiner

METHOD FOR PRODUCING WNT PROTEIN AND METHOD FOR STORING WNT PROTEIN

TECHNICAL FIELD

The present invention relates to a method for producing a Wnt protein and a method for storing a Wnt protein.

BACKGROUND ART

Wnt proteins are secretory proteins discovered as morphogens important for development and morphogenesis in higher organisms. In humans and mice, 19 types of Wnt proteins are known. Wnt proteins are recently recognized to be closely involved in bone formation (Non Patent Literature 1), cancer (Non Patent Literature 2), stem cell maintenance (Non Patent Literature 3), etc., and have drawn attention from not only biological and medical researchers but also pharmaceutical companies. Wnt proteins are strongly hydrophobic due to fatty acid (palmitoleic acid) modification of a specific serine residue (Non Patent Literature 4 and 5), so that they aggregate and denature in an aqueous solution. For this reason, Wnt proteins are widely known to be quite difficult to purify and store. On the other hand, this fatty acid modification is reportedly essential for the biological activity of Wnt proteins and involved in binding of Wnt proteins to Frizzled proteins, which serve as a receptor for Wnt proteins (Non Patent Literature 6). As just described above, Wnt proteins are currently the focus of considerable attention as a research target and tool, but the difficulty in purification and storage has been a major obstacle to studies related to Wnt proteins.

L cells (from mouse fibroblasts), a cell line stably expressing Wnt proteins such as Wnt3a and Wnt5a, have been established and are available from ATCC etc. (ATCC CRL-2647, ATCC CRL-2814, etc.). In the studies to assess Wnt activity, the culture supernatant of such Wnt protein-producing cells is used without purification in most cases. However, the concentrations of Wnt proteins in the culture supernatant cannot be determined, which makes it impossible to achieve quantitative analysis. Moreover, the secretion of Wnt proteins from the cells requires addition of fetal bovine serum to culture medium, and hence fetal bovine serum is inevitably contained in the above-described culture supernatant. For this reason, the culture supernatant of Wnt protein-producing cells cannot be used for assays which are susceptible to serum components (for example, cell differentiation assay etc.). In view of these problems, it would be desirable in various settings to use purified Wnt proteins.

Currently, in an established method for purifying Wnt proteins, the culture supernatant of cells stably expressing Wnt proteins is subjected to more than one step of chromatography (Non Patent Literature 7). Wnt proteins thus purified are commercially available from R&D Systems etc. However, the purification method of Non Patent Literature 7 involves very cumbersome and highly skilled operations as well as requires large-scale protein purification equipment. In addition, this method requires constant addition of a surfactant and a high-concentration salt in the course of purification steps. For this reason, when Wnt proteins purified as above are used, the contamination of Wnt proteins with the surfactant and the salt is a problem. Moreover, Wnt proteins purified by the method of Non Patent Literature 7 are difficult to store in such a manner that Wnt proteins can maintain their activity. In fact, commercially available purified Wnt proteins are expensive, but their activity is too low for the high price. That is, current techniques cannot provide highly purified Wnt proteins of known concentrations in a highly active state in physiological buffer. Therefore, if such Wnt proteins can be provided, many useful studies related to Wnt proteins would be exponentially accelerated.

CITATION LIST

Non Patent Literature

Non Patent Literature 1:
Baron & Kneissel, Nature Med., 19, 179 (2013)
Non Patent Literature 2:
Anastas & Moon, Nature Rev. Cancer, 13, 11 (2013)
Non Patent Literature 3:
Van Camp et al., Stem Cell Rev., 10, 207 (2014)
Non Patent Literature 4:
Willert et al., Nature, 423, 448 (2003)
Non Patent Literature 5:
Kishida et al., Mol. Cell. Biol., 24, 4487 (2004)
Non Patent Literature 6:
Janda et al., Science, 337, 59 (2012)
Non Patent Literature 7:
Willert, Methods Mol Biol., 468, 17 (2008)

SUMMARY OF INVENTION

Technical Problem

An object of the present invention is to provide a novel method for producing a Wnt protein having high Wnt activity and a method for storing a Wnt protein in a solution without loss of Wnt activity.

Solution to Problem

The present invention includes the following to achieve the above-mentioned object.
[1] A method for producing a Wnt protein from a culture product, the method comprising culturing Wnt protein-expressing cells in an afamin-containing culture medium to obtain the culture product, the method further comprising
(1) a step of performing affinity purification targeting afamin to obtain a Wnt protein from the culture product, and/or
(2) a step of performing affinity purification to obtain a Wnt protein in the form of a complex with afamin from the culture product.
[2] The method according to the above [1], wherein the method uses no surfactants.
[3] The method according to the above [1] or [2], wherein the Wnt protein produced is in the form of a complex with afamin and has Wnt activity.
[4] The method according to any one of the above [1] to [3], wherein the afamin-containing culture medium is a serum-containing culture medium.
[5] The method according to the above [4], wherein the serum is bovine serum.
[6] The method according to any one of the above [1] to [3], wherein the afamin-containing culture medium is a culture medium supplemented with purified afamin.
[7] The method according to the above [6], wherein the purified afamin is a recombinant afamin having an affinity tag.
[8] The method according to any one of the above [1] to [3], wherein the afamin-containing culture medium is a culture medium containing afamin secreted from afamin-expressing cells cultured therein.

[9] The method according to the above [8], wherein the afamin-expressing cells are cells expressing both the Wnt protein and afamin.

[10] The method according to the above [8] or [9], wherein the afamin secreted from the afamin-expressing cells is a recombinant afamin having an affinity tag.

[11] The method according to any one of the above [1] to [10], wherein the Wnt protein is selected from the group consisting of Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9a, Wnt10a, Wnt10b, Wnt11 and Wnt16.

[12] A method for storing a Wnt protein having Wnt activity in a surfactant-free solution, the method comprising storing a Wnt protein in the form of a complex with afamin.

[13] A Wnt protein-afamin complex having Wnt activity.

[14] A Wnt signaling activator containing a Wnt protein-afamin complex.

Advantageous Effects of Invention

The present invention provides a novel method for producing a Wnt protein and a method for storing a Wnt protein. According to the production method of the present invention, Wnt proteins having high Wnt activity can be produced in a simple and brief manner without use of special equipment. Moreover, according to the storage method of the present invention, Wnt proteins having Wnt activity can be stably stored in a surfactant-free solution without loss of the activity for a long period of time.

BRIEF DESCRIPTION OF DRAWINGS

FIG. 9 shows the results of gel filtration chromatography of a sample containing a surfactant and a sample not containing a surfactant. These samples were prepared by purifying W-Wnt3a from the culture supernatant of a W-Wnt3a stably expressing cell line (W-Wnt3a/HEK) using P20.1 antibody-sepharose, and adding or not adding the surfactant to the purified W-Wnt3a.

DESCRIPTION OF EMBODIMENTS

Method for Producing Wnt Protein

Figure 1:
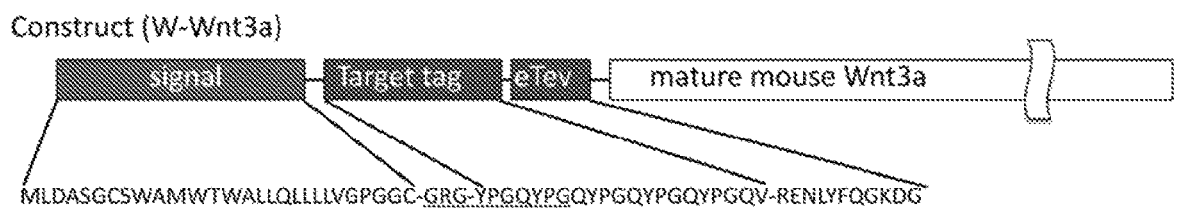
FIG. 1 shows the structure of a mouse Wnt3a fused with an affinity tag (W-Wnt3a).

The present invention provides a novel method for producing a Wnt protein. The production method of the present invention is a method for producing a Wnt protein from a culture product. The method comprises culturing Wnt protein-expressing cells in an afamin-containing culture medium to obtain the culture product, and further comprises (1) a step of performing affinity purification targeting afamin to obtain a Wnt protein from the culture product, and/or (2) a step of performing affinity purification to obtain a Wnt protein in the form of a complex with afamin from the culture product.

As long as a Wnt protein having Wnt activity can be produced from a culture product obtained by culturing Wnt protein-expressing cells in an afamin-containing culture medium, the production method of the present invention may comprise a step(s) other than steps (1) and (2), and the details of the step(s) are not limited.

The origin of the Wnt protein produced by the production method of the present invention is not particularly limited, and Wnt proteins of various organisms can preferably be produced. Preferred are Wnt proteins of mammals. Examples of the mammals include but are not limited to humans, mice, rats, cattle and pigs. Examples of the Wnt proteins of mammals include Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11 and Wnt16.

The Wnt protein-expressing cells may be of any origin (any biological species and cultured form) without particular limitations as long as they express a Wnt protein. The Wnt protein-expressing cells may be cells stably expressing a Wnt protein or cells transiently expressing a Wnt protein. For example, L cells stably expressing mouse Wnt3a (ATCC CRL-2647), L cells stably expressing mouse Wnt5a (ATCC CRL-2814), etc. can preferably be used. The Wnt protein-expressing cells can be produced by known recombinant techniques, that is, by inserting a DNA encoding the desired Wnt protein into a known expression vector, and introducing the resulting expression vector into appropriate host cells. The thus produced cells stably or transiently expressing a Wnt protein can preferably be used in the production method of the present invention. The nucleotide sequences of the genes encoding Wnt proteins can be obtained from known databases (e.g., GenBank). The GenBank accession numbers of the amino acid and nucleotide sequences of major Wnt proteins are shown in Table 1.

TABLE 1

| | Amino acid sequence | Nucleotide sequence |
|---|---|---|
| Mouse Wnt1 | NP_067254 | NM_021279 |
| Mouse Wnt2 | NP_076142 | NM_023653 |
| Mouse Wnt2b | NP_033546 | NM_009520 |
| Mouse Wnt3 | NP_033547 | NM_009521 |
| Mouse Wnt3a | NP_033548 | NM_009522 |
| Mouse Wnt4 | NP_033549 | NM_009523 |
| Mouse Wnt5a | NP_033550 | NM_009524 |
| Mouse Wnt5b | NP_033551 | NM_009525 |
| Mouse Wnt6 | NP_033552 | NM_009526 |
| Mouse Wnt7a | NP_033553 | NM_009527 |
| Mouse Wnt7b | NP_033554 | NM_009528 |
| Mouse Wnt8a | NP_033316 | NM_009290 |
| Mouse Wnt8b | NP_035850 | NM_011720 |
| Mouse Wnt9a | NP_647459 | NM_139298 |
| Mouse Wnt9b | NP_035849 | NM_011719 |
| Mouse Wnt10a | NP_033544 | NM_009518 |
| Mouse Wnt10b | NP_035848 | NM_011718 |
| Mouse Wnt11 | NP_033545 | NM_009519 |
| Mouse Wnt16 | NP_444346 | NM_053116 |
| Human Wnt1 | NP_005421 | NM_005430 |
| Human Wnt2 | NP_003382 | NM_003391 |
| Human Wnt2b | NP_078613 | NM_024494 |
| Human Wnt3 | NP_110380 | NM_030753 |
| Human Wnt3a | NP_149122 | NM_033131 |
| Human Wnt4 | NP_110388 | NM_030761 |
| Human Wnt5a | NP_003383 | NM_003392 |
| Human Wnt5b | NP_116031 | NM_032642 |
| Human Wnt6 | NP_006513 | NM_006522 |
| Human Wnt7a | NP_004616 | NM_004625 |
| Human Wnt7b | NP_478679 | NM_058238 |
| Human Wnt8a | NP_001287867 | NM_001300938 |
| Human Wnt8b | NP_003384 | NM_003393 |
| Human Wnt9a | NP_003386 | NM_003395 |
| Human Wnt9b | NP_003387 | NM_003396 |
| Human Wnt10a | NP_079492 | NM_025216 |
| Human Wnt10b | NP_003385 | NM_003394 |
| Human Wnt11 | NP_004617 | NM_004626 |
| Human Wnt16 | NP_476509 | NM_057168 |

The Wnt protein expressed in the Wnt protein-expressing cells may be a Wnt protein fragment, or have an amino acid sequence of Wnt protein and an additional amino acid sequence as long as Wnt activity is retained. The additional amino acid sequence is not particularly limited, and the examples include the amino acid sequences of affinity tags, etc. The amino acid sequence of Wnt protein does not have to be completely identical to that obtainable from databases such as GenBank. As long as Wnt activity is retained, the amino acid sequence of Wnt protein may be essentially identical to that obtainable from databases.

The amino acid sequence essentially identical to that of Wnt protein obtainable from databases such as GenBank is, for example, an amino acid sequence that is identical to that of Wnt protein obtainable from databases except for having deletion, substitution or addition of one to several amino acids. As used herein, "deletion, substitution or addition of one to several amino acids" means deletion, substitution or addition of an amino acid(s) of which the number substantially corresponds to the number of amino acids that can be deleted, substituted or added by a known method for preparing mutant peptides, such as site-directed mutagenesis (preferably 10 or less amino acids, more preferably 7 or less amino acids, and even more preferably 5 or less amino acids). In addition, the amino acid sequence essentially identical to that of Wnt protein obtainable from databases is, for example, an amino acid sequence that is at least 80% identical, preferably at least 85%, 90%, 92%, 95%, 96%, 97%, 98% or 99% identical to that of Wnt protein obtainable from databases.

The culture medium used for the culture of Wnt protein-expressing cells is not particularly limited, and can be selected from known culture media as appropriate for the type of the cells. The culture period is not particularly limited, and an appropriate culture period that does not need medium replacement is selected. Afamin is a glycoprotein belonging to the albumin family and is known to be present in blood and body fluid. However, the functions of afamin are poorly known. Serum, which is commonly added to cell culture medium, contains afamin of an animal from which the serum originates. Therefore, a serum-containing culture medium can preferably be used as the afamin-containing culture medium. The serum is not particularly limited as long as the serum is prepared for use in cell culture. Preferred is bovine serum. Examples of the bovine serum include fetal bovine serum, newborn calf serum and calf serum, and any of them can preferably be used. The amount of the serum added to culture medium is not particularly limited, and serum is added to culture medium at a concentration recommended for the culture of Wnt protein-expressing cells to be used.

Alternatively, a culture medium supplemented with purified afamin can be used as the afamin-containing culture medium. Purified afamin may be added to a serum-containing culture medium or a serum-free culture medium. The purified afamin may be a natural afamin purified by a known method or a recombinant afamin. The recombinant afamin can be produced by appropriate known recombinant techniques, that is, by inserting a DNA encoding afamin into a known expression vector, introducing the resulting expression vector into appropriate host cells for expression of a recombinant afamin, and purifying the recombinant afamin by a known purification method. The recombinant afamin may contain an affinity tag. The affinity tag is not particularly limited and can be selected from known affinity tags as appropriate. Preferred are affinity tags that are recognized by their specific antibodies. The specific examples include a FLAG tag, a MYC tag, an HA tag and a V5 tag. Other preferable examples of the affinity tag include the tags developed by the inventors, i.e., a tag having an amino acid sequence composed of 3 to 5 repeats of the amino acid sequence YPGQ (SEQ ID NO: 1) (hereinafter also called "TARGET tag") and a tag having the amino acid sequence GVAMPGAEDDVV (SEQ ID NO: 2) (hereinafter also called "PA tag").

The afamin-containing culture medium may be a culture medium containing afamin secreted from afamin-expressing cells cultured therein. The afamin-expressing cells may be cells expressing both a Wnt protein and afamin or cells expressing afamin. The afamin secreted from afamin-expressing cells may be a natural afamin expressed from an endogenous afamin gene of the afamin-expressing cells or a recombinant afamin expressed from an introduced afamin expression vector in the afamin-expressing cells. Cells which express and secrete a recombinant afamin can be produced by appropriate known recombinant techniques. In the case where cells expressing both a Wnt protein and afamin are used as the afamin-expressing cells, the desired culture product can be obtained by culturing the cells. In the case where cells expressing afamin but not a Wnt protein are used as the afamin-expressing cells, the desired culture product can be obtained by co-culturing cells expressing a Wnt protein and the cells expressing afamin.

The afamin may be from any organism. Preferred are afamins of mammals. Examples of the mammals include humans and cattle. The amino acid sequences of afamins of major mammals and the nucleotide sequences of the genes encoding the afamins can be obtained from known databases such as GenBank. For example, the amino acid sequence of human afamin is registered under the accession number AAA21612, and the nucleotide sequence of the gene encoding human afamin is registered under the accession number L32140. The amino acid sequence of bovine afamin is registered under the accession number DAA28569, and the nucleotide sequence of the gene encoding bovine afamin is registered under the accession number GJ060968.

In the case where the afamin-containing culture medium is prepared by adding purified afamin to a serum-free culture medium, the amount of the purified afamin added is not particularly limited and is preferably about 1 µg/mL to about 50 µg/mL, more preferably about 20 µg/ml to about 50 µg/mL. Addition of purified afamin to a serum-containing culture medium or to a culture medium containing afamin secreted from afamin-expressing cells increases the afamin concentration in the culture medium, enabling an increased yield of the Wnt protein. In the case of the addition of purified afamin to a serum-containing culture medium, it is preferable that the amount of the purified afamin added is appropriately set so that the Wnt protein can be obtained in a higher yield than that without the addition of the purified afamin.

Culturing Wnt protein-expressing cells in an afamin-containing culture medium provides a culture product containing the Wnt protein expressed in the Wnt protein-expressing cells. The production method of the present invention is for producing the Wnt protein from the culture product. The culture product may be culture supernatant, a mixture of culture supernatant and cultured cells, a mixture of culture supernatant and cell lysate, or the like, and can be prepared by a known method. Since Wnt proteins are secretory proteins, they are usually secreted into culture medium. Therefore, the culture product is preferably a culture product containing culture supernatant, and more preferably culture supernatant obtained by removal of the cells.

The inventors have found that, during the culture of Wnt protein-expressing cells in an afamin-containing culture medium, the Wnt protein secreted from the Wnt protein-expressing cells is coupled to afamin in the culture medium in a one-to-one manner to form a complex. Based on this finding, the step (1) in the production method of the present invention is characterized in that affinity purification targeting afamin is performed to obtain the Wnt protein from the culture product. The method for affinity purification targeting afamin is not particularly limited and can be selected from known affinity purification methods as appropriate. The specific examples include a method using an anti-afamin antibody, a method using a recombinant afamin having an affinity tag, a method using a biotin-labeled afamin, and a method using an afamin-binding molecule other than antibodies (including low-molecular-weight compounds).

In the method using an anti-afamin antibody, the antibody may be a polyclonal or monoclonal antibody. The antibody may be a whole antibody molecule or an antibody fragment (for example, Fab, F(ab')$_2$, Fab', Fv, scFv, etc.) capable of specifically binding to an antigen of interest. The polyclonal antibody can be obtained, for example, in the following manner. An antigen (afamin or a fragment thereof) is dissolved in PBS and if needed mixed with an appropriate amount of a usual adjuvant (for example, Freund's complete adjuvant) to prepare an immunogen, and a mammal (a mouse, a rat, a rabbit, a goat, a horse, etc.) is immunized with the immunogen. The immunization method is not particularly limited, but preferred is subcutaneous or intraperitoneal injection given once or repeated several times at appropriate intervals, for example. After the immunization, blood collection from the immunized animal, serum separation and purification of polyclonal antibody fractions are performed in the usual manner to give a polyclonal antibody of interest. The monoclonal antibody can be obtained by fusing immune cells (for example, splenocytes) obtained from the above-mentioned immunized mammal with myeloma cells to produce a hybridoma, culturing the hybridoma, and collecting an antibody from the culture product. As the monoclonal antibody, a recombinant one can also be produced by recombinant techniques, specifically by cloning an antibody gene from the hybridoma, inserting the gene into a suitable vector, and transfecting the vector into host cells. The phage display method can also be used for production of the monoclonal antibody.

In the method using an anti-afamin antibody, an antibody immobilized to a support is preferably used. The support used for the immobilization of an antibody is not particularly limited and can be selected from known supports as appropriate. For example, sepharose (GE Healthcare), Affi-Gel (BIO-RAD), etc. can preferably be used. The method for immobilizing an antibody to a support is not particularly limited and can be selected as appropriate for the type of the support etc. For example, in the case where sepharose is used as the support, an antibody is dialyzed against a coupling buffer and then mixed with CNBr-activated Sepharose (GE Healthcare) at room temperature for about 1 to 2 hours to give an antibody immobilized to the sepharose.

In the method using an anti-afamin antibody, a column protocol which uses a column packed with the above-described immobilized antibody as well as a batch protocol which involves mixing the above-described immobilized antibody with a sample for coupling in a suspension can be used. In the former protocol, the immobilized antibody is packed into a column, a culture product obtained by culturing Wnt protein-expressing cells in an afamin-containing culture medium is passed through the column, and the anti-afamin antibody is allowed to capture a Wnt protein-afamin complex formed in the culture product. In the latter protocol, about 100 μL of the immobilized antibody is gently mixed with 10 mL of a culture product to allow the anti-afamin antibody to capture a Wnt protein-afamin complex formed in the culture product, and the mixture is then packed into a column.

In the method using a recombinant afamin having an affinity tag, the optimal affinity tag system can be selected from known affinity tag systems according to the affinity tag used. In the method using a biotin-labeled afamin, for example, an avidin-immobilized support, a streptavidin-immobilized support, etc. can be used. In the method using an afamin-binding factor (e.g., proteins and low-molecular-weight compounds), a support to which the factor has been immobilized can be used. In these methods, both the column protocol and the batch protocol as described above can be used as with the method using an anti-afamin antibody.

The production method of the present invention is characterized by isolating a Wnt protein, which is poorly water soluble and prone to inactivation due to aggregation, in the form of a complex with afamin. The inventors have found that a Wnt protein secreted from Wnt protein-expressing cells is coupled to afamin in culture medium in a one-to-one manner to form a stable complex. As a result, by purifying a Wnt protein in the form of a complex with afamin, they have succeeded in obtaining the Wnt protein in a soluble state without loss of its high activity. Since the production method of the present invention provides a Wnt protein in a state of being protected by afamin, neither a surfactant nor a high-concentration salt needs to be added to the Wnt protein during and after a purification step. Therefore, the present invention can provide a purified Wnt protein in a surfactant- and salt-free state.

The step (2) in the production method of the present invention involves a procedure for eluting a Wnt protein-afamin complex captured in affinity purification targeting afamin or the Wnt protein. The method for eluting the captured Wnt protein-afamin complex is not particularly limited and can be selected as appropriate for the affinity purification method used. For example, in the case where the TARGET tag developed by the inventors is used, a suitable elution buffer is an elution buffer containing, as an eluent, a peptide containing the amino acid sequence of the N-terminal region of the human thrombin receptor PAR4 (for example, PAR4-C8 peptide (PRGYPGQV, SEQ ID NO: 3) used in the Examples). Although the concentration of the peptide is not particularly limited, it is preferably about 0.1 mg/mL to about 1 mg/mL, for example. In the case where the PA tag developed by the inventors is used, a suitable elution buffer is an elution buffer containing, as an eluent, a peptide containing the amino acid sequence of the PLAG domain of human podoplanin (PA14). In addition to these affinity tags, other affinity tags including many commercial ones can also be used for attachment to afamin or Wnt proteins. Among the elution methods suitable for each affinity purification system, the methods with elution conditions that do not disrupt the interaction between afamin and Wnt proteins can be widely used.

From the Wnt protein-afamin complex captured in affinity purification targeting afamin in step (1), only the Wnt protein can be separated and purified. That is, an appropriately selected eluent is used to allow disruption of the interaction between the Wnt protein and afamin in the complex, but not disruption of the interaction between afamin and, for example, an antibody immobilized to an affinity support, thereby achieving the separation of only the Wnt protein and the purification thereof. Examples of such an eluent include CHAPS (3-(3-cholamidopropyl)dimethylammonio-1-propanesulphonate), CHAPSO (3-(3-cholamidopropyl)dimethylammonio-2-hydroxypropanesulfonate), cholic acid, deoxycholic acid and Triton X-100 (polyethylene glycol p-(1,1,3,3-tetramethylbutyl)-phenyl ether). In the case where CHAPS is used as the eluent, a preferable concentration of CHAPS is in the range of about 0.3% (w/v) to about 3% (w/v) in an appropriate buffer. After elution, the Wnt protein is concentrated as appropriate by, for example, the same method as described in Non Patent Literature 7, and then can be used in a subsequent test.

The Wnt activity of the obtained Wnt protein-afamin complex or Wnt protein can be evaluated by, for example, TCF reporter assay. The TCF reporter assay is a simple method for the evaluation of the strength of Wnt activity. Specifically, a luciferase gene fused to a sequence for binding of T-cell factor (TCF), which is a transcription factor specifically activated upon the initiation of Wnt signal transduction in cells, is introduced, and the luminescence in the luciferase-mediated reaction is measured as an index of the strength of Wnt activity (Molenaar et al., Cell, 86, 391 (1996)). Evaluation methods other than the TCF reporter assay include a method using western blotting for the quantitative determination of intracellular β-catenin, which is stabilized upon the initiation of Wnt signal transduction in cells (Shibamoto, et al., Genes to cells, 3, 659 (1998)). Moreover, in the case where the Wnt protein is a Wnt protein that transduces a signal to cells via what is called the non-canonical pathway, for example, Wnt5a, Wnt activity can foe evaluated by, for example, a method involving monitoring the phosphorylation of the intracellular adaptor protein Dvl2 (Kikuchi et al., EMBO J. 29, 3470 (2010)).

The production method of the present invention can provide a Wnt protein having Wnt activity as a single protein or in a Wnt protein-afamin complex. In the production method of the present invention, a Wnt protein having Wnt activity can efficiently be obtained in a single step of affinity purification without use of special equipment. That is, the production method of the present invention is significantly superior to the conventional method (Non Patent Literature 7) in that a Wnt protein having Wnt activity can be produced in a very simple, brief and easy manner. Moreover, the Wnt activity of the Wnt protein-afamin complex obtained by the production method of the present invention has been confirmed by the inventors to be 10-fold or more higher in terms of the specific activity than a commercial product (manufactured by R&D Systems) produced by the conventional method (Non Patent Literature 7) (see Example 5 and FIG. 11).

Method for Storing Wnt Protein

The present invention provides a novel method for storing a Wnt protein. The storage method of the present invention is characterized by storing a Wnt protein in the form of a complex with afamin, thereby enabling the storage of the Wnt protein in a surfactant-free solution without a significant loss of Wnt activity. Preferable examples of the surfactant-free solution include various buffers which are commonly used for protein storage. The specific examples include phosphate buffer (20 mM phosphate, 150 mM NaCl, pH 7.0) and HEPES buffer (20 mM HEPES, 150 mM NaCl, pH 7.2). The storage temperature is preferably room temperature or lower, and more preferably about 4° C. or lower. For long-term storage, freezing storage at −80° C. or lower is preferred. The inventors have confirmed that a Wnt protein having Wnt activity in the form of a Wnt protein-afamin complex can be stored in a dissolved state in PBS at 4° C. for at least one month or more without loss of the activity.

Wnt Protein-Afamin Complex

The present invention provides a Wnt protein-afamin complex having Wnt activity. The Wnt protein-afamin complex of the present invention is formed in a culture product (for example, culture supernatant) obtained by culturing Wnt protein-expressing cells in an afamin-containing culture medium. The method for purifying the Wnt protein-afamin complex formed in the culture product is not particularly limited. As described above for the production method of the present invention, affinity purification targeting afamin, affinity purification targeting a Wnt protein, affinity purification targeting an affinity tag attached to afamin or a Wnt protein, etc. can preferably be used.

The origin of the Wnt protein forming the Wnt protein-afamin complex of the present invention is not particularly limited, and Wnt proteins of various organisms can preferably be used. Preferred are Wnt proteins of mammals. Examples of the mammals include but are not limited to humans, mice, rats, cattle and pigs. Examples of the Wnt proteins of mammals include Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11 and Wnt16.

The afamin forming the Wnt protein-afamin complex of the present invention is not particularly limited and may be a natural afamin or a recombinant afamin. The origin of the afamin is not particularly limited, and afamins of various organisms can preferably be used. Preferred are afamins of mammals. Examples of the mammals include but are not limited to humans and cattle.

The Wnt protein-afamin complex of the present invention has been confirmed to have 10-fold or more higher specific activity than that of the commercial Wnt protein (for example, manufactured by R&D Systems). Moreover, the Wnt protein-afamin complex of the present invention can be stored in a dissolved state in a surfactant-free solution at 4° C. for at least one month or more without loss of activity. The Wnt protein-afamin complex of the present invention likely contributes to exponential acceleration of many useful studies in various research fields related to Wnt proteins.

Wnt Signaling Activator

The present invention provides a Wnt signaling activator containing a Wnt protein-afamin complex. The Wnt protein-afamin complex of the present invention has high Wnt activity and hence can efficiently activate Wnt signaling. The Wnt signaling activator of the present invention can be a very useful tool in basic research which attempts to clarify the molecular mechanisms of the developmental and differentiation processes in animals. In addition, since the Wnt signaling activator of the present invention is free from surfactants, it can be used as a culture additive for iPS cells, ES cells, etc. based on the ability or Wnt proteins for stem cell maintenance and directed differentiation. This means that the Wnt signaling activator is also applicable to research and development related to regenerative medicine using such pluripotent stem cells. Moreover, the Wnt signaling activator can be used for other applications including screening for antibodies and compounds targeting Wnt proteins in the development of cancer therapeutic agents etc.

The present invention further includes the following.
(a) A method for activating Wnt signaling, the method comprising using a Wnt protein-afamin complex.
(b) Use of a Wnt protein-afamin complex for production of a Wnt signaling activator.
(c) A Wnt protein-afamin complex for use in activation of Wnt signaling.

EXAMPLES

Hereinafter, the present invention will be illustrated in detail by examples, but the present invention is not limited thereto.

Example 1

Identification of Protein which Forms a Complex with Wnt3a in Culture Supernatant 1. L-3a Cells L cells stably expressing mouse Wnt3a (L-3a cells), which had been established by Professor Shinji Takada from Okazaki Institute for Integrative Bioscience, were kindly provided by the professor (Shibamoto et al., Genes to Cells, 3, 659 (1998)).

2. W-Wnt3a/HEK Cells

The structure of a mouse Wnt3a fused with an affinity tag (hereinafter called "W-Wnt3a") is shown in FIG. 1. As shown in FIG. 1, W-Wnt3a has a structure in which the sequence represented by SEQ ID NO: 5 is attached to at the N-terminus of mouse Wnt3a mature protein (residues 19 to 352 of GenBank ACCESSION P27467, SEQ ID NO: 4). The sequence represented by SEQ ID NO: 5 contains the signal sequence of human prolactin (SEQ ID NO: 6), a TARGET tag sequence of 21 residues (SEQ ID NO: 7), and an eTEV sequence of 11 residues (SEQ ID NO: 8). The GRG between the signal sequence of human prolactin and the TARGET tag sequence is an artificial sequence resulting from insertion of a restriction enzyme site (NotI) for cloning. First, a DNA encoding the signal sequence of human prolactin, a DNA encoding the TARGET tag sequence, a DNA encoding the eTEV sequence and a DNA encoding the mouse Wnt3a mature protein were joined together to prepare a W-Wnt3a construct, and this construct was inserted into the expression vector pEBMulti-Hyg (Wako Pure Chemical Industries).

A W-Wnt3a stably expressing cell line was prepared as follows.
1) On the day before transfection, HEK293S_GnT1− cells (kindly provided by Dr. G. Khorana) were seeded on 10-cm dishes and cultured overnight (37° C., 5% CO$_2$).
2) On the following day, the cells grown to 50 to 60% confluency were transfected with the W-Wnt3a expression vector. That is, the plasmid DNA and a transfection reagent (X-tremeGENE HP, Roche) were mixed and added to the cells. The ratio of plasmid DNA:Xtreme was 1:3. As a negative control, an empty vector without hygromycin resistance was similarly added to the cells in another dish.
3) On the day after the transfection, the culture medium was removed and replaced with culture medium containing 0.2 mg/mL of hygromycin B (Gibco, 10687-010) as a selection antibiotic.
4) The culture medium was replaced with a fresh one (containing hygromycin) every 3 to 5 days until the cells were well grown. The cells as the negative control died completely by 6 days after the transfection.
5) At 23 days after the transfection, the culture supernatant of well-grown cells was subjected to western blotting using an anti-Wnt3a antibody (kindly provided by Professor Shinji Takada from Okazaki Institute for Integrative Bioscience) for confirmation of the expression of Wnt3a.

3. Cell Culture Methods (3-1) Culture of L-3a Cells

DMEM/F12_1:1 (Gibco, 11320-033) was used as culture medium for L-3a cells, DMEM/F12_1:1 was supplemented with 10% (v/v) fetal calf serum (FCS), 0.5% penicillin-streptomycin (SIGMA, P4458) and 1.4 g/L D-glucose as additives. For maintenance and passage of the cells, the cells were diluted about 20-fold every 3 to 4 days.

(3-2) Culture of W-Wnt3a/HEK

DMEM (WAKO, 043-30085) was used as culture medium for W-Wnt3a/HEK. DMEM was supplemented with 10% (v/v) FCS, 0.5% penicillin-streptomycin (SIGMA, P4458) and 1% NEAA (SIGMA, M7145) as additives, and with 0.2 mg/mL hygromycin B (Gibco, 10687-010) as a selection antibiotic. For maintenance and passage of the cells, the cells were diluted about 10- to 20-fold every 3 to 4 days.

4. Western Blotting

Western blotting was performed according to the following protocol.

Dilution of the culture supernatant was performed as described in the next section "5. TCF Reporter Assay of Culture Supernatant".
1) Five microliters of the culture supernatant was subjected to electrophoresis (SDS-PAGE), and separated proteins were transferred to a PVDF membrane.
2) The PVDF membrane was blocked and then stained with a primary antibody (5 µg/mL biotin-anti-Wnt3a antibody/TBST) for 2 hours. The primary antibody used was a purified anti-Wnt3a antibody labeled using a biotinylation reagent (PIERCE, EZ-Link NHS-Lc-Biotin). The composition of TBST was 20 mM Tris-HCl, 150 mM NaCl and 0.05% Tween 20 at pH 8.0.
3) The PVDF membrane was stained with a secondary antibody (0.4 µg/mL streptavidin-HRP/TBST) for 1 hour.
4) Chemiluminescence was produced using a western blotting detection reagent (GE, ECL Prime) and imaged (GE, LAS 4000 mini).

Figure 2:
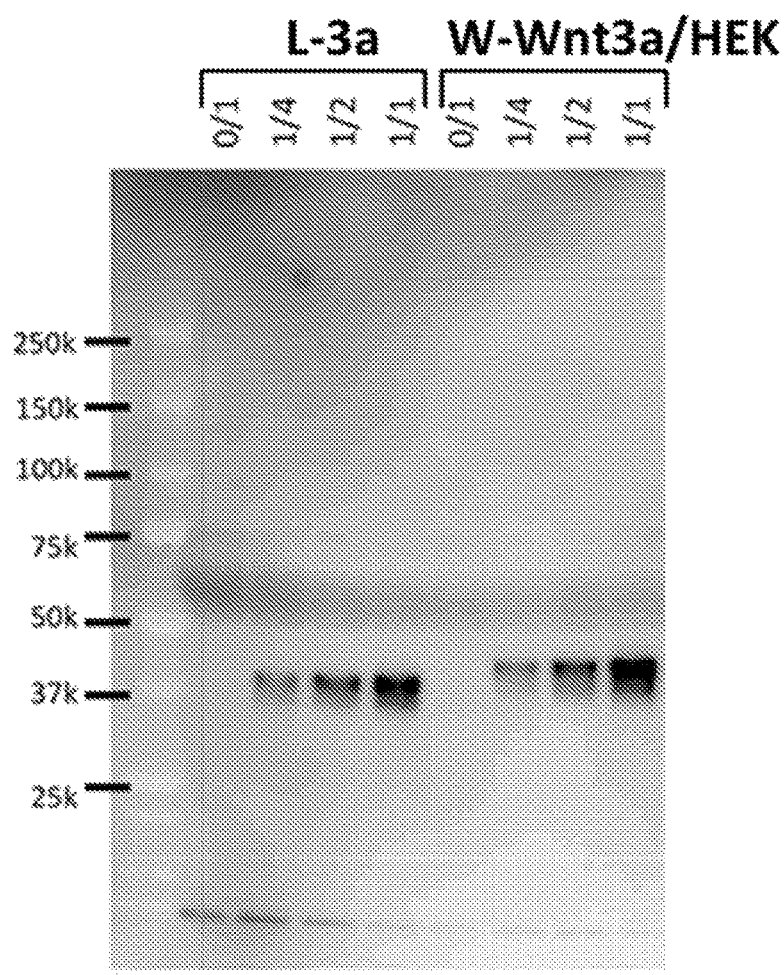
FIG. 2 shows the results of western blotting for the detection of Wnt3a protein in the culture supernatants of L-3a cells and W-Wnt3a/HEK cells.

The results of the western blotting are shown in FIG. 2. As shown in FIG. 2, the secretion of the Wnt3a protein into the supernatant was confirmed in both types of cells. The results of the serial dilution show that the established stably expressing cell line (W-Wnt3a/HEK) has a Wnt3a-producing ability comparable to that of L-3a cells, which are used as the global standard. It should be noted that the Wnt3a protein produced by W-Wnt3a/HEK has a slightly greater molecular weight than that of the wild-type Wnt3a protein secreted by L-3a cells due to the N-terminal tag sequence.

5. TCF Reporter Assay of Culture Supernatant

TCF reporter assay was performed according to the following procedure.

(5-1) Transfection of Reporter Gene

HEK293T cells were transfected with the TOPflash plasmid (firefly luciferase reporter plasmid containing a TCF-binding site). In consideration of the influence of transfection efficiency, the *Renilla* plasmid (*Renilla* luciferase reporter plasmid) was co-transfected with the TOPflash plasmid for normalization. Specifically, HEK293T cells cultured on a 24-well plate were transfected with a mixture of 50 ng of TOP_DNA and 5 ng of *Renilla*_DNA per well. The above-mentioned X-tremeGENE HP (Roche) was used as the transfection reagent in such an amount that the ratio of DNA:Xtreme was 1:3.

(5-2) Addition of Supernatant Containing an Expressed Wnt3a

On the day after the transfection, the culture medium was gently removed and replaced with a supernatant containing an expressed Wnt3a. The supernatant containing an expressed Wnt3a was a supernatant obtained by culturing each of the Wnt3a stably expressing cell lines for 3 to 4 days, harvesting the culture medium at 80 to 90% cell confluency, and centrifuging the harvested culture medium. For dilution of the supernatant containing an expressed Wnt3a the culture supernatant of HEK293T (conditioned medium) was used.

(5-3) Signal Detection

Dual-Luciferase Reporter Assay System (Promega) was used as the reagent for signal detection. On the day after the addition of the supernatant containing an expressed Wnt3a, the culture supernatant was removed so gently as to avoid cell detachment. The culture vessel was washed with 500 µL of phosphate buffered saline (PBS), and the cells were lysed with 100 µL of Passive Lysis Buffer (×1) supplied in the kit. The cell lysate was centrifuged, and the resulting supernatant was applied to the wells of a 96-well white plate (NUNC, 236105) at 8 µL/well. The supernatant was reacted with 40 µL of Luciferase Assay Reagent II supplied in the kit, and immediately after the start of the reaction, the luminescence in the firefly luciferase reaction (firefly) was measured with a plate reader. After the measurement, 40 µL of Stop & Glo Reagent (×1) supplied in the kit was added to quickly quench the luminescence in the firefly luciferase reaction, and the luminescence in the *Renilla* luciferase reaction (renilla) was measured. The level of activity was calculated by the following formula.

$$\text{Activity} = (\text{firefly/renilla}) - (\text{firefly (BG)/renilla (BG)})$$

Figure 3:
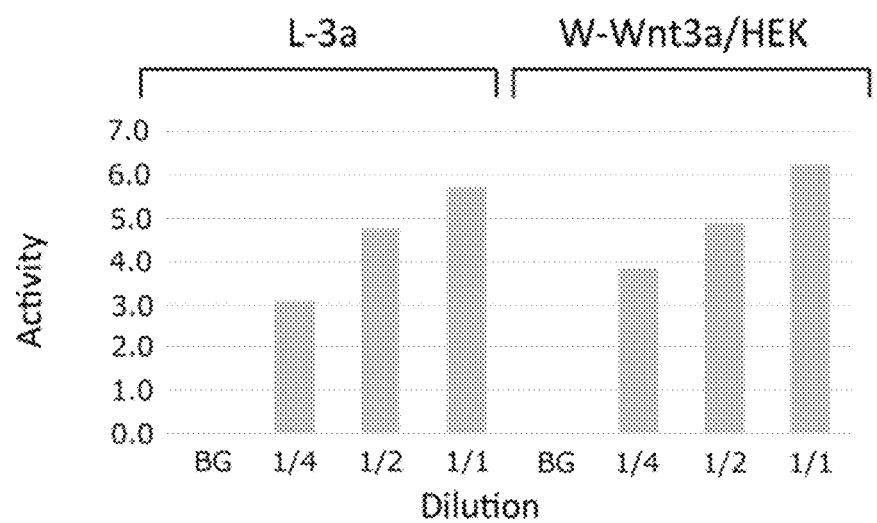
FIG. 3 shows the results of TCF reporter assay using the culture supernatants of L-3a cells and W-Wnt3a/HEK cells as samples.

The results of the TCF reporter assay are shown in FIG. 3. As shown in FIG. 3, the culture supernatants of both types of cells exhibited Wnt signaling activity with a similar concentration dependency. These results demonstrate that the N-terminally tagged Wnt3a (W-Wnt3a) has a bioactivity comparable to that of the wild-type, tag-free Wnt3a.

6. Purification of W-Wnt3a Using Affinity Tag System

The W-Wnt3a stably expressing cell line (W-Wnt3a/HEK) was cultured in a dish or a multilayered flask for 5 to 7 days, and the culture medium was harvested. After the culture medium was centrifuged, the supernatant was passed through a 0.22-µm filter. To 220 ml of the culture supernatant, 3 mL of P20.1 antibody-sepharose was added, and the mixture was rotated end over end at 4° C. for 3 hours. The mixture was loaded into an empty column to collect the sepharose. Here, the P20.1 antibody specifically recognizes the above-mentioned TARGET tag sequence and is a monoclonal antibody produced by mouse-mouse hybridoma P20.1, which was internationally deposited under the accession number FERM BP-11061 (see WO 2009-096112).

The sepharose collected in the column was washed with 3 mL of Tris buffered saline (20 mM Tris-HCl, 150 mM NaCl, pH 7.5), and the wash solution was harvested (wash fraction). Five cycles of washing were performed, and thus the fractions designated as wash 1 to 5 were obtained. Subsequently, elution was performed with 3 ml of a peptide solution (0.2 mg/ml, PAR4-C8 peptide/TBS), and the eluate was harvested (elute fraction). Ten cycles of elution were performed, and thus the fractions designated as elute 1 to 10 were obtained. Ten microliters each was taken from wash 1 to 5 and elute 1 to 10, and subjected to electrophoresis (SDS-PAGE) under non-reducing conditions. After the electrophoresis, the gel was stained with Coomassie Brilliant Blue (CBB).

Figure 4:
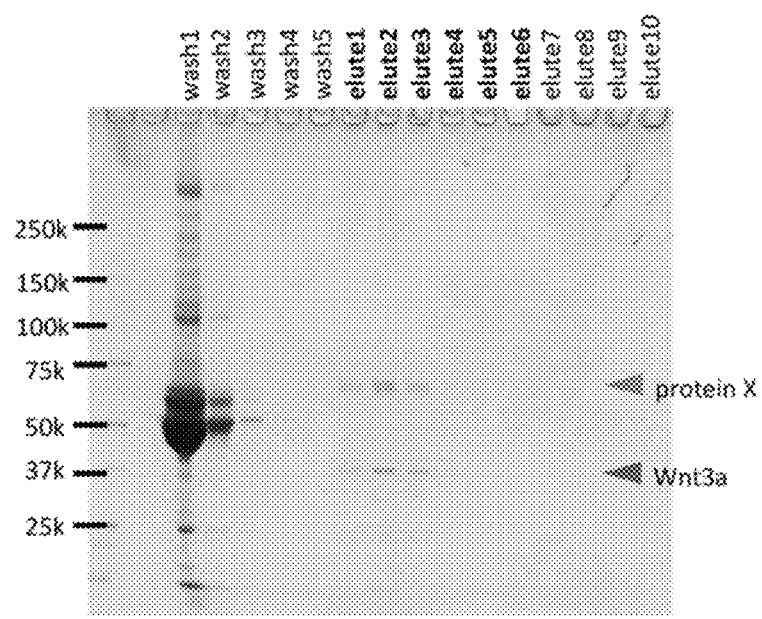
FIG. 4 shows the results of electrophoresis of wash fractions (wash 1 to 5) and elute fractions (elute 1 to 10) obtained in the course of the purification of W-Wnt3a using P20.1 antibody-sepharose.

The results of the electrophoresis are shown in FIG. 4. As shown in FIG. 4, serum proteins contained in the culture medium were abundant in the wash fractions, but such nonspecific bands almost completely disappeared after 5 cycles of washing. In the elute fractions, specifically purified 37-kDa Wnt3a was observed. In these elute fractions, an unidentified protein with a molecular weight of about 65 kDa (protein X) was also eluted.

7. Analysis of N-terminal Amino Acid Sequences of Purified Proteins

The elute fractions obtained above were concentrated, and the N-terminal amino acid sequences of the 37-kDa band and the 65-kDa band were determined by the Edman method. As a result, the following sequences were determined.

37 kDa: GRGYPGQYPG (SEQ ID NO: 9)
65 kDa: LPTQPQDVDD (SEQ ID NO: 10)

The former sequence corresponds to the region containing a partial sequence of the TARGET tag and a partial sequence of the original vector (underlined in FIG. 1) in a signal sequence-cleaved form of W-Wnt3a. Therefore, the 37-kDa protein was identified as W-Wnt3a as expected. The latter sequence was searched against a database, and as a result, found to have 100% identity to the deduced N-terminal sequence of a mature form of a bovine serum protein, afamin (residues 22 to 31 of GenBank ACCESSION NP_001179104, afamin precursor [Bos taurus]). In addition, the molecular weight was almost the same as that of bovine afamin. Therefore, the 65-kDa protein was strongly suspected as bovine afamin.

8. Identification of Bovine Afamin by Peptide Mass Fingerprinting (PMF) Analysis To confirm the results of the N-terminal sequence analysis, protein X was subjected to PMF analysis (analysis using a combination of protease digestion and mass spectrometry). The PMF analysis was outsourced to SHIMADZU TECHNO-RESEARCH. The results of the PMF analysis showed that protein X matches bovine afamin (GenBank ACCESSION NP_001179104, afamin precursor [Bos taurus]) with very high reliability (Mascot score: 311). In conclusion, protein X was identified as bovine afamin. Afamin is a glycoprotein with a molecular weight of about 66,000 belonging to the albumin family and is present at a concentration of about 30 µg/mL in human serum (Lichenstein et al., J. Biol. Chem. 269, 18149 (1994)). As with serum albumin, afamin is also reported to bind to various lipids, particularly vitamin E (Jerkovic et al., J. Proteome Res. 4, 889 (2005)), but the physiological roles are unknown. Since protein X was constantly present in the Wnt3a samples obtained by the affinity tag-based purification, protein X was considered to be in the form of a stable complex with Wnt3a. Since the cells used for the expression of Wnt3a are human cells, i.e., HEK cells, the bovine afamin obviously originates from fetal calf serum contained in the culture medium. That is, a possible theory is that, upon secretion from the cells, Wnt3a binds to afamin in the culture medium to form a complex, which is harvested by affinity purification.

Example 2

Complex Formation of Wnt3a with Recombinant Human Afamin

To clarify whether a complex of a Wnt protein and afamin forms only in the presence of bovine serum or a Wnt protein is capable of binding to afamin without any mediation of other factors, a recombinant human afamin was prepared and the binding activity of the recombinant human afamin to a Wnt protein was examined.

1. Production of Recombinant Human Afamin

Human afamin full-length cDNA was kindly provided by Dr. Luc Belanger from Laval University, Canada. An expression construct for a human afamin fused with a PA tag (Fujii et al., Protein Expr. Purif., 95, 240 (2014)) at the C-terminus (hAFM-PA) was transiently expressed using Expi293 System available from Life Technologies Inc. The expressed recombinant human afamin was purified from the culture supernatant using NZ-1-sepharose in a single step. The purified sample was dissolved in PBS and filter-sterilized for use in the following experiments.

2. Expression Experiment of Wnt3a in the Presence of Recombinant Human Afamin

1) The Wnt3a expressing cells (L-3a and W-Wnt3a/HEK) were seeded on a 12-well plate and incubated in a serum-containing culture medium overnight to allow the cells to adhere to the plate.

2) On the following day, the culture medium was removed gently and then replaced with a culture medium with serum (5% (v/v) FCS) or without serum (0% FCS).

3) The purified recombinant human afamin was added to the serum-free culture medium at a concentration of 0, 5, 10, 20 or 30 µg/mL.

4) After 5 days of culture, the culture supernatant was subjected to electrophoresis and subsequent western slotting using an anti-Wnt3a antibody.

Figure 5:
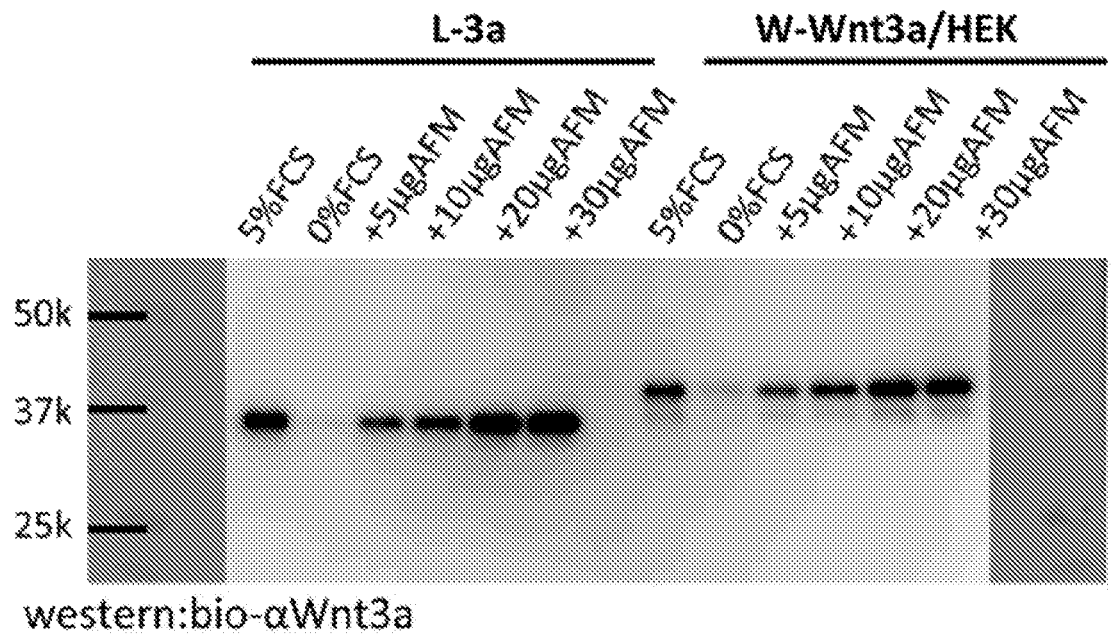
FIG. 5 shows the results of western blotting for the detection of Wnt3a in the culture supernatants of Wnt3a expressing cells (L-3a and W-Wnt3a/HEK) cultured in a serum-free culture medium supplemented with recombinant human afamin.

The results of western blotting are shown in FIG. 5. As shown in FIG. 5, Wnt3a was not secreted into the serum-free culture medium, but in the serum-free culture medium supplemented with the purified recombinant human afamin, the secretion of Wnt3a increased in an afamin concentration dependent manner.

In an additional experiment, after the culture of W-Wnt3a/HEK in the culture medium with 5% (v/v) FCS or in the culture medium supplemented with the recombinant human afamin instead of serum, W-Wnt3a was purified from the culture supernatant by the same method as described in "6. Purification of W-Wnt3a Using Affinity Tag System" of Example 1 and then subjected to electrophoresis.

Figure 6:
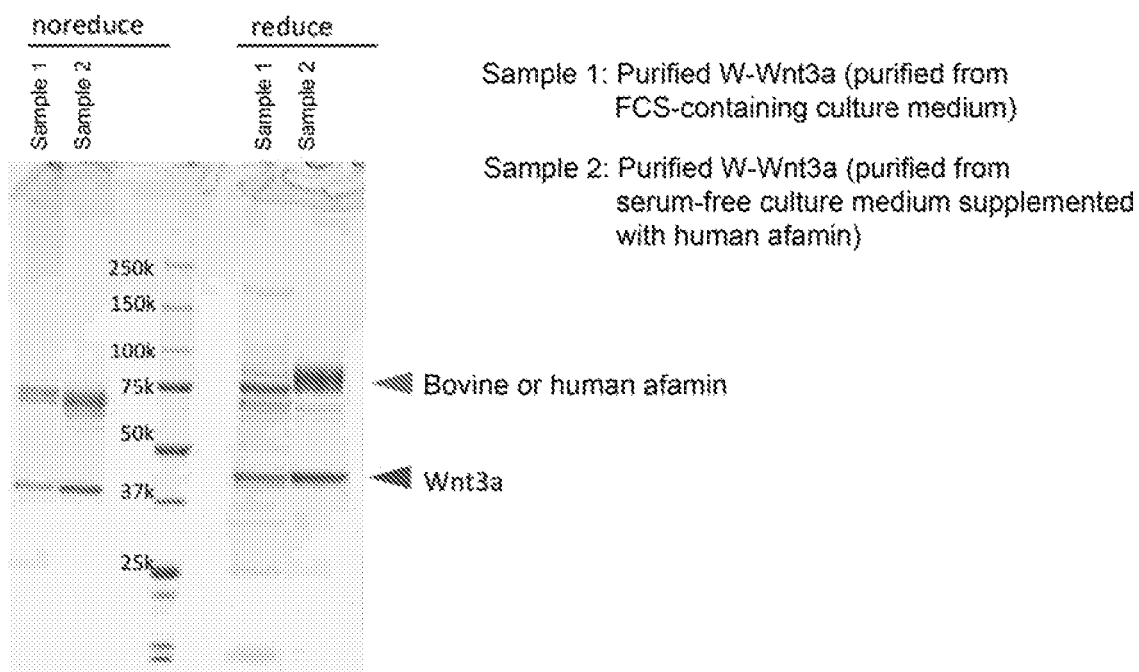
FIG. 6 shows the results of electrophoresis of W-Wnt3a purified using P20.1 antibody-sepharose from the culture supernatant of W-Wnt3a/HEK cultured in a culture medium containing 5% (v/v) fetal calf serum or in a culture medium supplemented with recombinant human afamin instead of serum.

The results of the electrophoresis are shown in FIG. 6. As shown in FIG. 6, from the culture supernatant of the culture medium supplemented with the recombinant human afamin, W-Wnt3a was purified in the form of a complex with the human afamin instead of bovine afamin.

Example 3

Immunoprecipitation of Wnt3a-Afamin Complex Using Anti-Bovine Afamin Antibodies

1. Production of Recombinant Bovine Afamin

Bovine afamin full-length cDNA was prepared by DNA synthesis by reference to the sequence of Bos taurus afamin (AFM), mRNA, GenBank ACCESSION NM_001192175. In the same manner as in the case of human afamin, an expression construct for a C-terminally PA-tagged bovine afamin (bAFM-PA) was prepared from the cDNA and transiently expressed using Expi293 System available from Life Technologies Inc. The expressed recombinant bovine afamin was purified from the culture supernatant using NZ-1-sepharose in a single step. After cleavage of the tag by TEV protease, the resulting bovine afamin was subjected to gel filtration purification and used as an antigen for antibody production.

2. Production of Anti-Bovine Afamin Polyclonal and Monoclonal Antibodies

Polyclonal antiserum was prepared from rabbits by the usual method. Monoclonal antibodies which recognize native bovine afamin were prepared from BALB/c mice and P3U1 myeloma cells by the usual method. Clone screening was performed by ELISA using antigen-coated plates, and finally, 6 clones were established.

3. Immunoprecipitation of Afamin in Bovine Serum by Established Monoclonal Antibodies The six established monoclonal antibodies (B11, B72, B91, B115, B212 and B213) and the polyclonal rabbit antibody were used with CNBr-activated Sepharose 4B (GE Healthcare) to prepare antibody-immobilized resins. Each of these resins was mixed with a culture medium containing 10% (v/v) fetal calf serum (FCS) and incubated at 4° C. for 1 hour. After washing with TBS, proteins eluted with SDS sample buffer were subjected to SDS electrophoresis.

Figure 7:
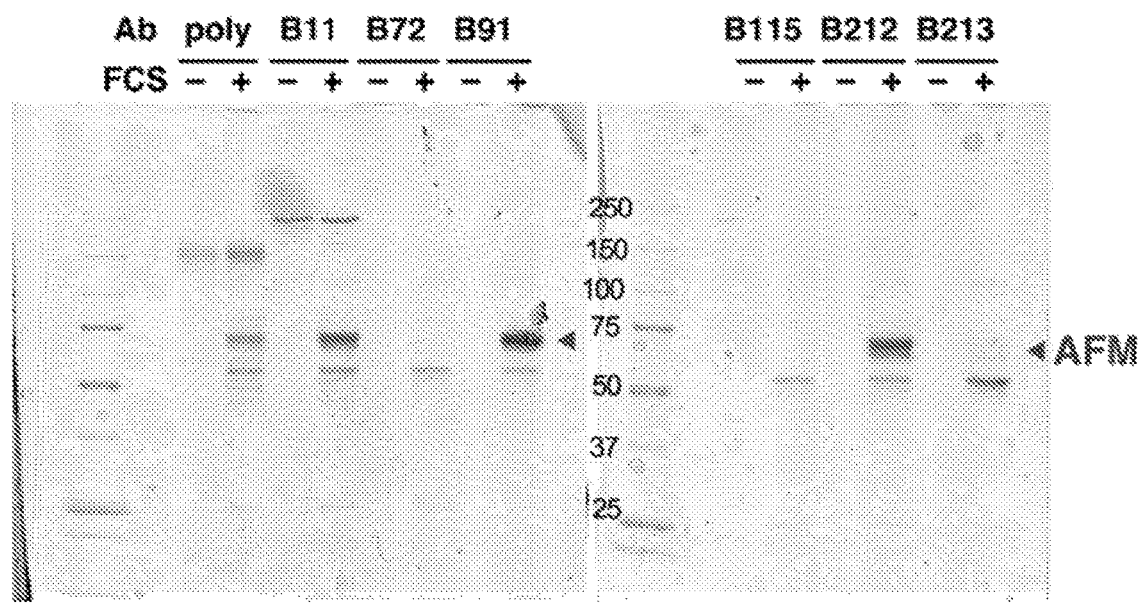
FIG. 7 shows the results of electrophoresis to confirm the presence of afamin in the immunoprecipitates obtained from fetal calf serum using an anti-bovine afamin polyclonal or monoclonal antibodies.

The results of the electrophoresis are shown in FIG. 7. As shown in FIG. 7, in addition to the polyclonal antibody, B11, B91 and B212 precipitated an about 70-kDa band from the serum. Therefore, these antibodies were found to be capable of recognizing bovine afamin in a native state.

4. Immunoprecipitation of Wnt3a-Afamin Complex Using Anti-Bovine Afamin Monoclonal Antibody The Wnt3a expressing cells (L-3a and W-Wnt3a/HEK) were cultured for 3 days, and the supernatants were harvested. To 1 mL of each supernatant, 20 µL of a sepharose with an anti-bovine afamin monoclonal antibody (clone number B91, hereinafter called "B91") immobilized thereto was added, and the mixture was rotated end over end for 3 hours. The sepharose was precipitated by centrifugation, and the supernatant was removed. After the sepharose was washed 3 times with 1 mL of TBS, 30 µL of SDS sample buffer was added, and elution was performed under heating at 95° C. for 2 minutes. Eight microliters of the eluate was subjected to electrophoresis under reducing conditions, and separated proteins were stained with ORIOLE. In a separate experiment, 4 µL of the eluate was subjected to electrophoresis, and western blotting using an anti-Wnt3a antibody was performed (see Example 1).

Figure 8:
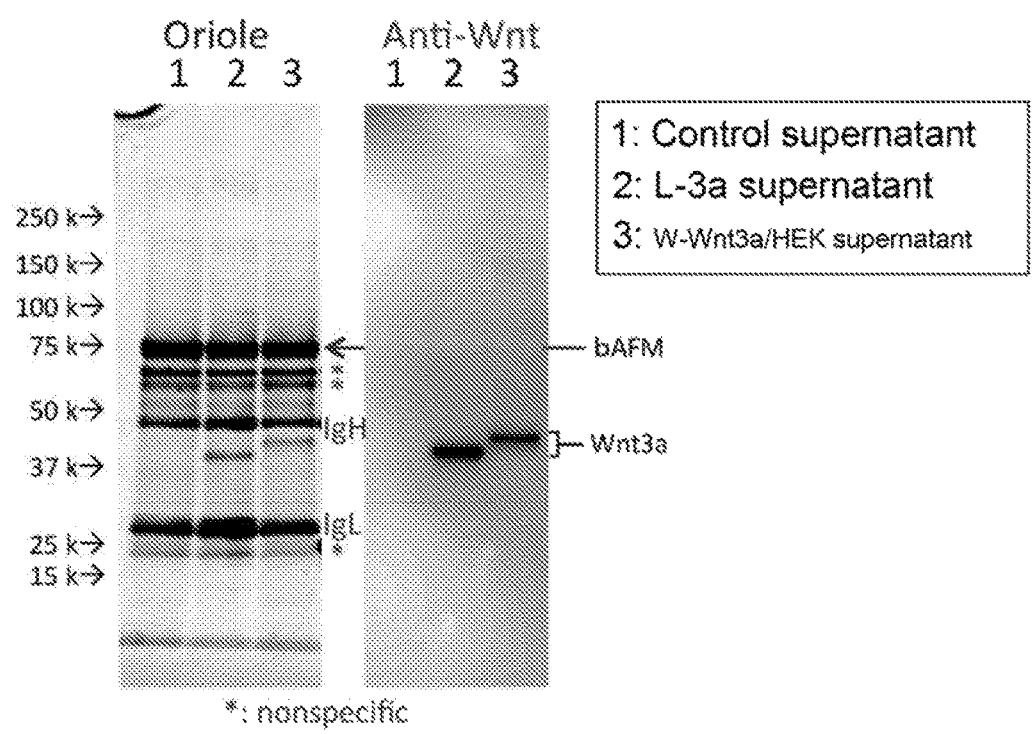
FIG. 8 shows the results of electrophoresis and western blotting of the immunoprecipitates obtained using an anti-bovine afamin monoclonal antibody from the culture supernatants of Wnt3a expressing cells (L-3a and W-Wnt3a/HEK) cultured in a culture medium containing fetal calf serum.

The results of the electrophoresis (left) and the western blotting (right) are shown in FIG. 8. As is clear from FIG. 8, B91 precipitated bovine afamin (the arrowed band in electrophoresis) from the culture medium containing serum, and also precipitated Wnt3a from the culture supernatant of the Wnt3a expressing cells (the bands in western blotting). These results show that afamin forms a complex with Wnt3a regardless of the presence or absence of the tag and that the Wnt3a-afamin complex can be purified using B91.

Example 4

Gel Filtration Chromatography of Wnt3a-Afamin Complex

To confirm the formation of a stable 1:1 complex of afamin and Wnt3a, gel filtration chromatography, which is a protein separation technique based on molecular size, was performed. At the same time, the influence of the surfactant CHAPS (3-(3-cholamidopropyl)dimethylammonio-1-propanesulphonate) was also examined.

1. Sample Preparation

The W-Wnt3a stably expressing cell line (W-Wnt3a/HEK) was cultured, and W-Wnt3a was purified from 1 L of the culture supernatant using P20.1-sepharose by the same method as described in Example 1. The collected fractions were concentrated to 1 mL. The concentrate was used as a CHAPS (−) sample. Separately, to this sample, CHAPS was added at a final concentration of 1% (w/v), and this was allowed to stand on ice for 1 hour or more to prepare a CHAPS (+) sample.

2. Gel Filtration Chromatography

AKTA FPLC chromatography system (GE Healthcare) was used for gel filtration. The column used was Superdex 200 10/300 GL. The buffer used in the case of CHAPS (−) was PBS, and the buffer used in the case of CHAPS (+) was PBS supplemented with CHAPS at a final concentration of 1% (w/v). The flow rate was set to 0.5 mL/min, and fractions were collected every 250 µL.

Figure 9:
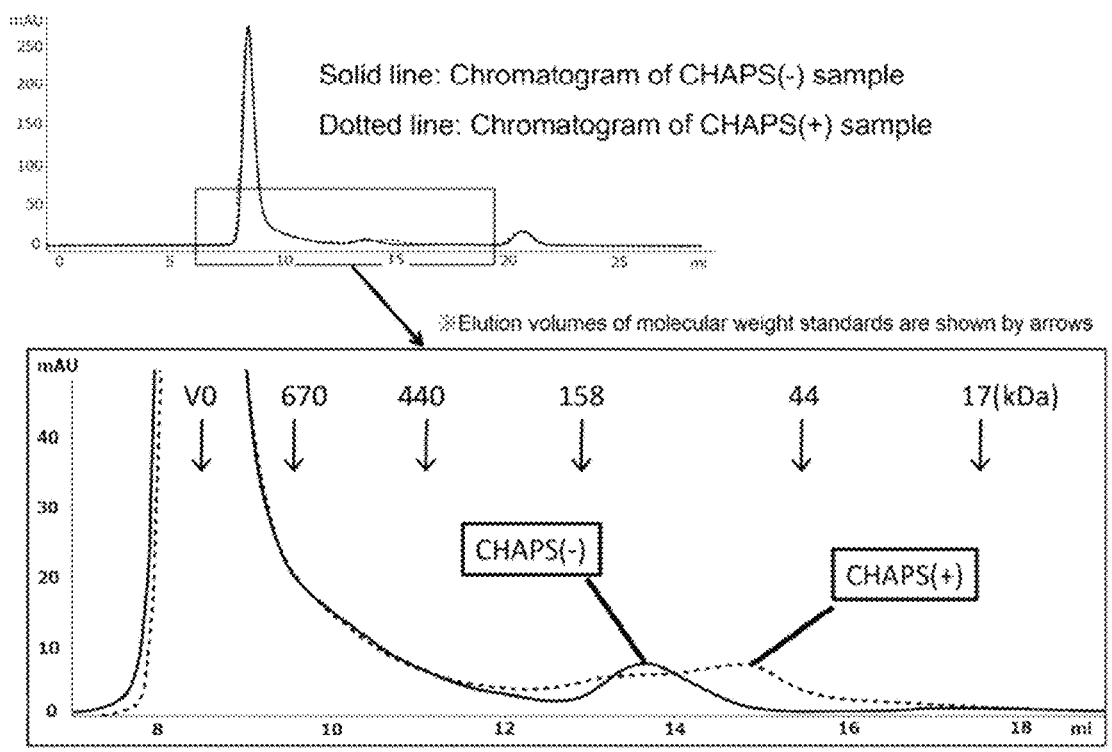

The results of the gel filtration chromatography are shown in FIG. 9. As shown in FIG. 9, a great peak was observed in the void volume (Vo) corresponding to the high-molecular-weight region, and another peak was observed at the 13- to 15-mL elution volume. Based on the elution volumes of the molecular weight standards, the peaks of the CHAPS (−) sample and the CHAPS (+) sample were found to represent molecular weights of about 101 kDa and about 55 kDa, respectively.

3. Analysis of Gel Filtration Fractions

Figure 10:
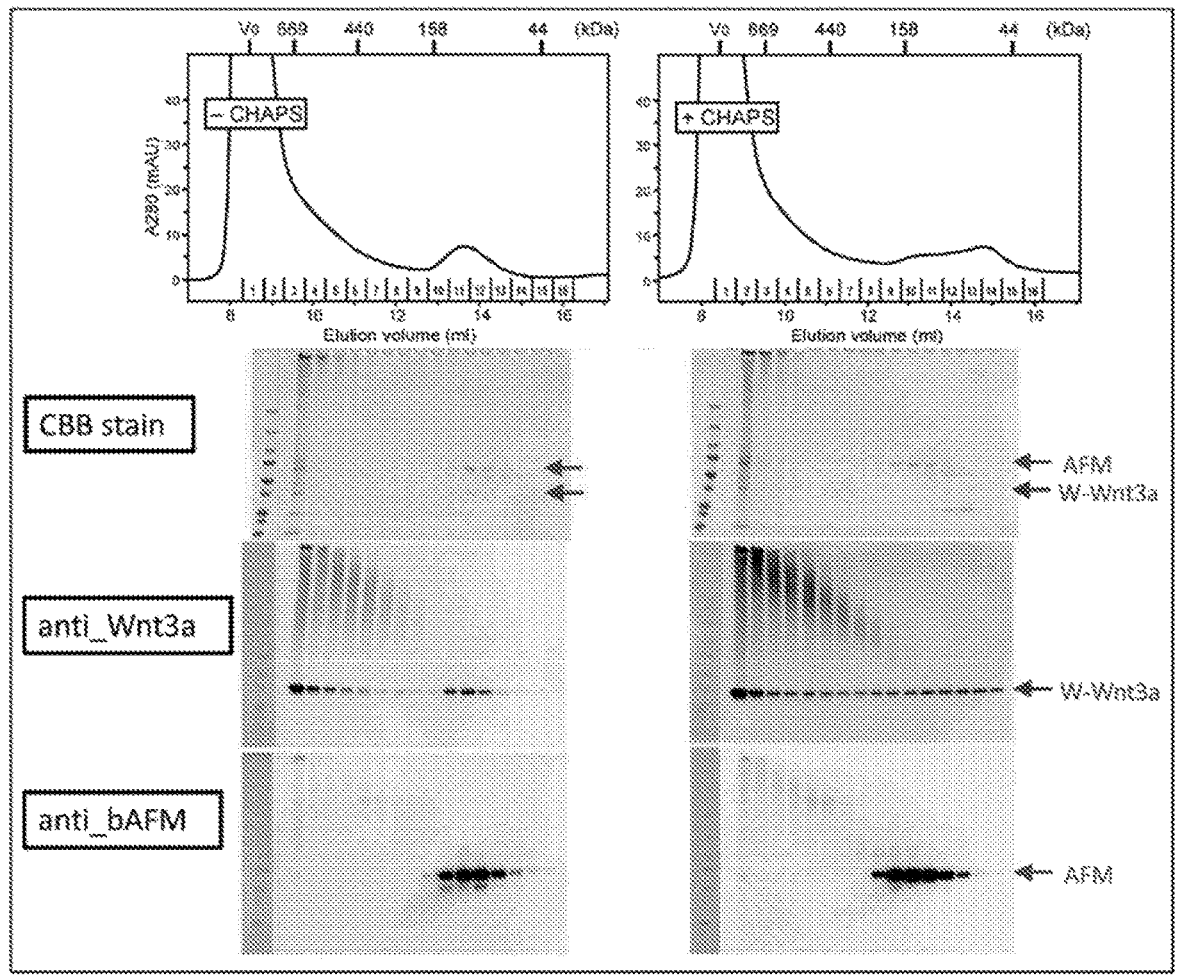
FIG. 10 shows the results of Coomassie staining, western blotting using an anti-Wnt3a antibody and western blotting using an anti-bovine afamin antibody after electrophoresis of 16 fractions each obtained in the course of the gel filtration chromatography of the two samples in FIG. 9.

Among the collected gel filtration fractions, the fractions 1 to 16 shown in the upper panels of FIG. 10 were selected, and 10 µL each of the selected fractions were subjected to electrophoresis under non-reducing conditions. After the electrophoresis, CBB staining, western blotting using an anti-Wnt3a antibody and western blotting using an anti-bovine afamin antibody (rabbit) were separately performed. The western blotting was performed according to the method described in Example 1. However, for detection of bovine afamin, the rabbit anti-bovine afamin polyclonal antibody prepared in Example 3 was used at 27 µg/mL/TBST as the primary antibody, and anti-rabbit-HRP/TBST was used at 0.4 µg/mL as the secondary antibody.

The results are shown in FIG. 10. The left panels of FIG. 10 show the results of the CHAPS (−) sample, and the right panels show the results of the CHAPS (+) sample. As shown in FIG. 10, in the absence of CHAPS, afamin and Wnt3a behaved as a complex, which was observed in fractions 10 to 12. Based on the predicted molecular weight of the complex (101 kDa), the 37-kDa Wnt3a and the 66-kDa afamin were considered to be coupled in one-to-one manner. The Wnt3a protein was present also in the high-molecularweight region corresponding to fractions 1 to 5, but afamin was not present in these fractions. Only the Wnt3a which formed a complex with afamin behaved as a monodisperse molecule. On the other hand, in the gel filtration chromatogram in the presence of CHAPS, the elution volume of afamin was almost the same as that in the CHAPS (−) conditions, while Wnt3a was distributed broadly from the high-molecular-weight region to the monodisperse region and had no peak that overlaps with that of afamin.

These results show the following: Wnt3a forms a complex with afamin and thereby behaves as a water-soluble monodisperse protein; the interaction between Wnt3a and afamin is disrupted by surfactants such as CHAPS; and Wnt3a dissociated from the complex is likely to be polymerized. In a possible hypothesis, Wnt3a which is not coupled to afamin is incorporated into a lipoprotein complex as already reported (Newmann et al., Traffic, 10, 334 (2009)), and forms covalent bonds or non-covalent bonds with another Wnt3a molecule or other proteins to form high molecular aggregates.

Example 5

Wnt3a Possesses Activity in the Form of Complex with Afamin

A commercial product, Recombinant Mouse Wnt3a (High Purity) (R&D Systems, code: 1324-WNP-010/CF), was purchased and was used as a Wnt3a protein. As a Wnt3a-afamin complex, the Wnt3a-afamin complex purified using P20.1-sepharose in Example 1 was used. The Wnt3a protein or the Wnt3a-afamin complex was diluted with PBS so that the Wnt3a concentration would be 20 µg/mL to prepare a "1-fold diluted stock solution". The stock solution was diluted 1/3, 1/10, 1/30 and 1/100 with PBS. Each of these diluted solutions was mixed with a fresh culture medium (DMEM supplemented with 10% (v/v) FCS) at a ratio of 1:9, and the mixture was added to HEK293T cells which had been transfected with the TOPflash plasmid on the previous day. The TCF reporter assay was performed in the same manner as in Example 1.

Figure 11:
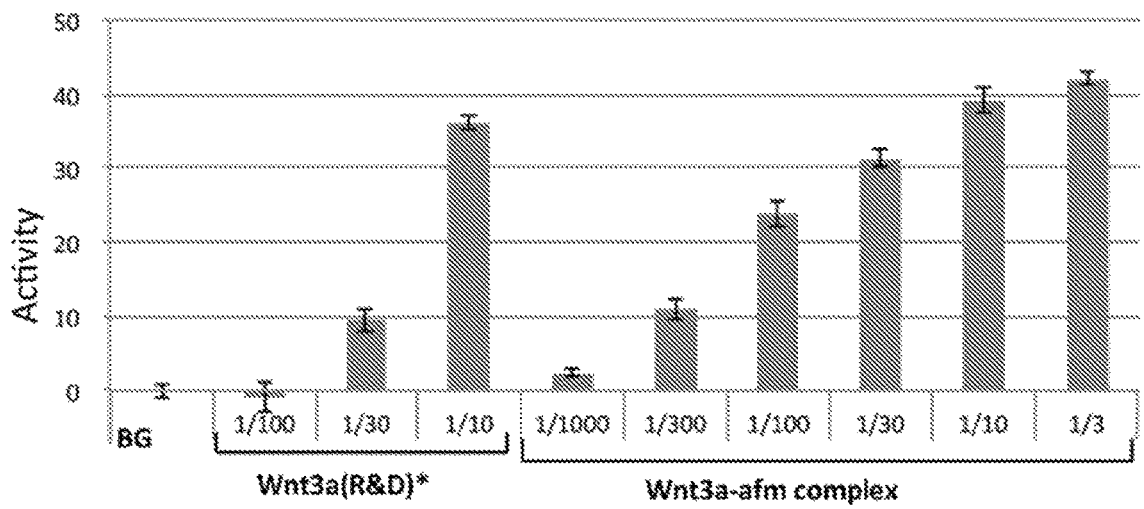
FIG. 11 shows the results of TCF reporter assay to confirm the activity of a Wnt3a-afamin complex.

The results of the TCF reporter assay are shown in FIG. 11. As shown in FIG. 11, the Wnt3a-afamin complex activated the TCF reporter in a concentration dependent manner. These results show that Wnt3a exerts bioactivity (Wnt activity) even in a state of being coupled to afamin. Moreover, the commercial Wnt3a protein with the highest purity (priced at about 180,000 yen/10 µg) needed to be used at a concentration of 0.67 µg/mL or more (corresponding to 1/30 in FIG. 11) to exert activity, while the Wnt3a-afamin complex can exert activity at 0.02 µg/mL or more (corresponding to 1/1000 in FIG. 11). These results show that the production method of the present invention can provide an active Wnt3a protein having a 10-fold or more higher specific activity than that of the commercial product.

Example 6

Storage Stability of Wnt3a-Afamin Complex

The purified Wnt3a-afamin complex (concentration: about 10 µg/mL in terms of Wnt3a) was dialyzed against PBS. The dialyzed complex was stored as it was at 4° C. for 12 days, or at −80° C. for the same period after flash freezing. The frozen sample was thawed on the day before the measurement of the activity. The sample stored at 4° C. and the sample stored at −80° C. were separately diluted 1/3, 1/10, 1/30 and 1/100 with PBS. Each of these diluted solutions was mixed with a fresh culture medium (DMEM supplemented with 10% (v/v) FCS) at a ratio of 1:9, and the mixture was added to HEK293T cells which had been transfected with the TOPflash plasmid on the previous day. The TCF reporter assay was performed in the same manner as in Example 1.

Figure 12:
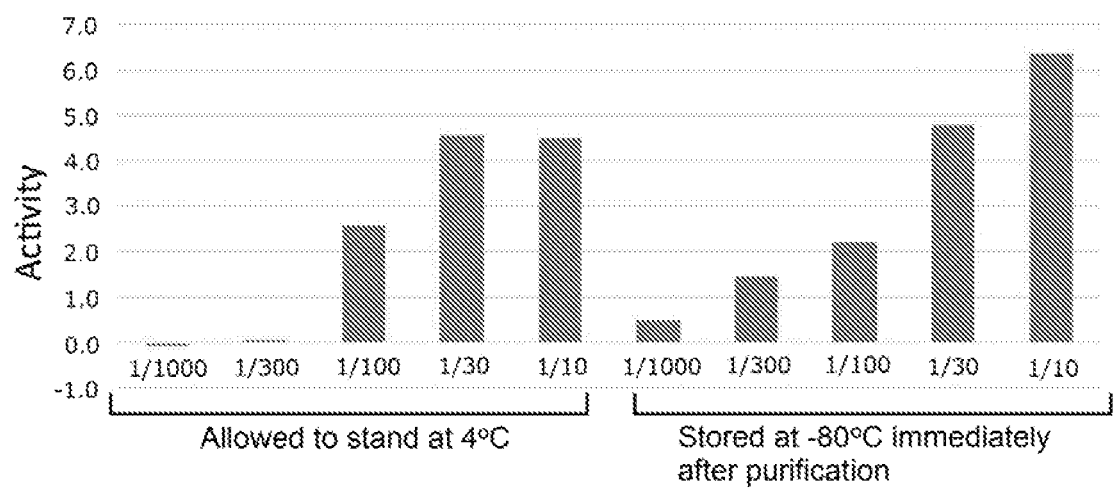
FIG. 12 shows the results of TCF reporter assay to confirm the activity of a Wnt3a-afamin complex stored at 4° C. or −80° C.

The results of the TCF reporter assay are shown in FIG. 12. As shown in FIG. 12, the Wnt3a-afamin complex stored at 4° C. and the Wnt3a-afamin complex stored at −80° C. exhibited Wnt activity with almost the same concentration dependency. These results show that Wnt3a purified in the form of a complex with afamin can be stored at 4° C. in the absence of surfactants while kept active. Additionally, the inventors confirmed that the Wnt3a-afamin complex did not lose Wnt activity at all after stored at 4° C. even for 1 month.

Example 7

Purification of Wnt5a-Afamin Complex

1. Purification of Wnt5a-Afamin Complex
A cell line stably expressing a Wnt5a fused with a TARGET tag at the N-terminus (hereinafter called "W-Wnt5a") (W-Wnt5a/HEK cells) was prepared according to the method described in "2. W-Wnt3a/HEK Cells" or Example 1. W-Wnt5a was purified from the culture supernatant of the W-Wnt5a stably expressing cell line according to "6. Purification of W-Wnt3a Using Affinity Tag System" of Example 1. The specific procedure was as follows. To 1 L of the culture supernatant, 10 mL of P20.1-sepharose was added, and the mixture was rotated end over end at 4° C. for 4 hours. Five cycles of washing with 10 mL of TBS were performed (wash 1 to 5), followed by 10 cycles of elution with 10 mL of a peptide solution (0.2 mg/mL PAR4-C8 peptide/TBS) (elute 1 to 10). Ten microliters each of the collected fractions were subjected to electrophoresis under non-reducing conditions. After the electrophoresis, the gel was stained with CBB.

Figure 13:
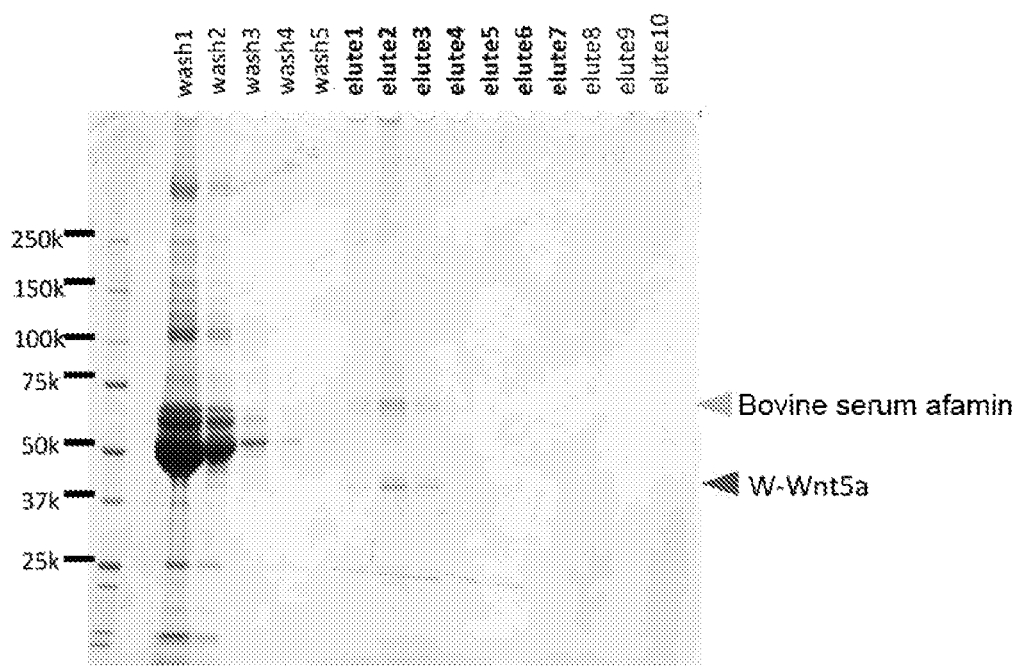
FIG. 13 shows the results of electrophoresis of wash fractions (wash 1 to 5) and elute fractions (elute 1 to 10) obtained in the course of the purification of W-Wnt5a using P20.1 antibody-sepharose.

The results of the electrophoresis are shown in FIG. 13. As shown in FIG. 13, the sample purified from the supernatant by affinity chromatography contained Wnt5a protein and serum afamin, and they behaved in the exact same manner as in the case of Wnt3a (see FIG. 4). These results show that afamin binds not only to Wnt3a but also to other Wnt proteins to form a complex.

2. Gel Filtration Analysis of Wnt5a-Afamin Complex
The Wnt5a-afamin complex purified above was concentrated, and the concentrate was subjected to gel filtration chromatography in the same manner as in Example 4. The column used was Superdex 200 10/300 GL. The buffer used was HBS (20 mM HEPES, 150 mM NaCl, pH 7.5), and the flow rate was set to 0.5 mL/min. Fractions were collected every 250 µL.

Figure 14:
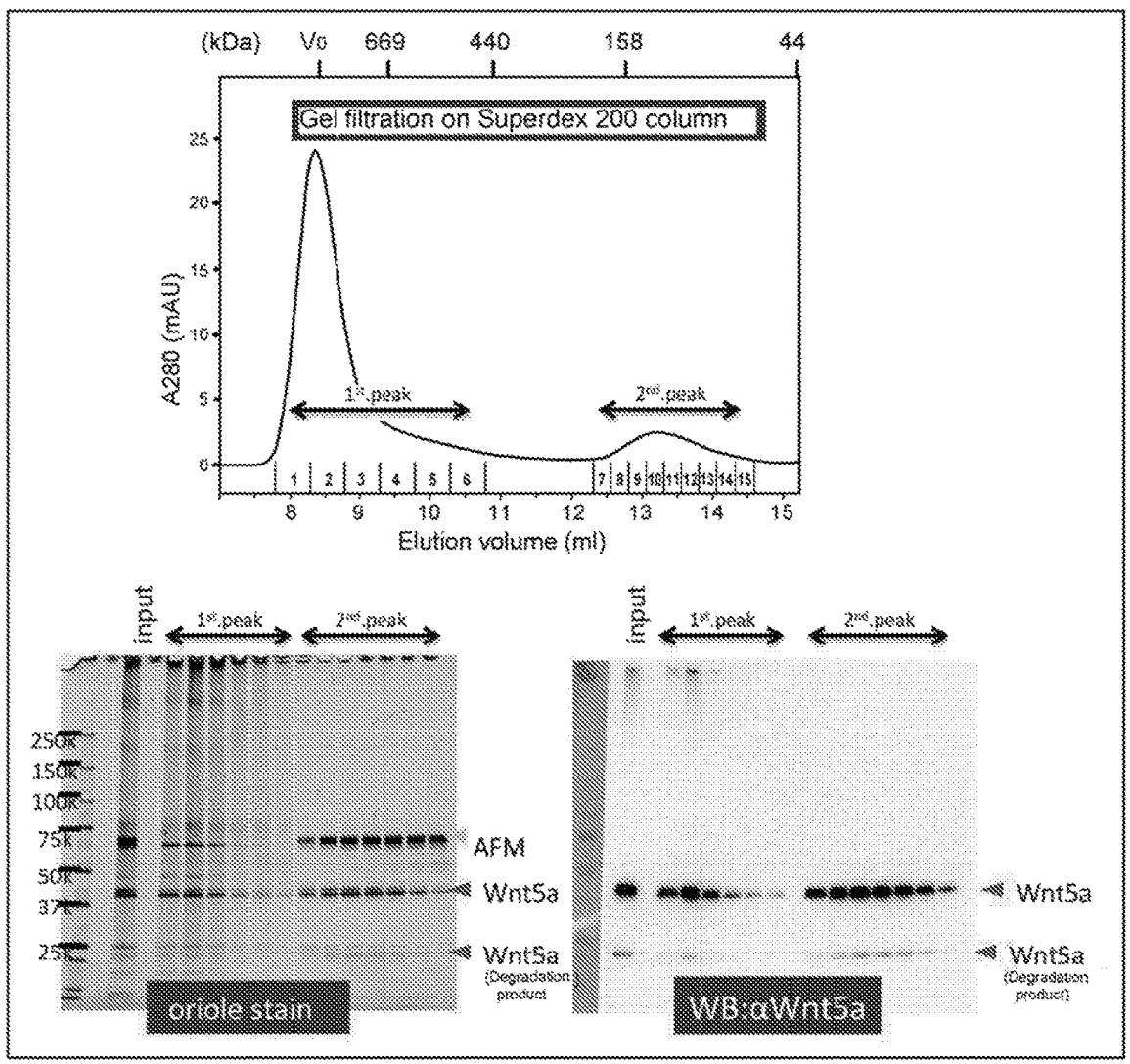
FIG. 14 shows the gel filtration chromatogram of a sample purified from the culture supernatant of a W-Wnt5a stably expressing cell line (W-Wnt5a/HEK) using P20.1 antibody-sepharose, and also shows the results of ORIOLE staining and western blotting using an anti-Wnt5a antibody after electrophoresis of gel filtration fractions 1 to 6 from the first chromatographic peak and gel filtration fractions 7 to 15 from the second chromatographic peak.

The results of the gel filtration chromatography are shown in FIG. 14. As shown in the upper panel of FIG. 14, the first peak appeared in the high-molecular-weight region close to the void volume, and the second peak appeared at an elution volume of about 13 mL. Among the collected gel filtration fractions, the fractions 1 to 15 shown in the upper chart of FIG. 14 were selected, and 10 µL each of the selected fractions were subjected to electrophoresis under non-reducing conditions. After the electrophoresis, ORIOLE staining (lower left panel of FIG. 14) and western blotting using an anti-Wnt5a antibody (lower right panel of FIG. 14) were separately performed. From these results, a band of a molecular weight of about 40 kDa was identified as Wnt5a.

Also shown was that, as with Wnt3a, Wnt5a is coupled to bovine serum afamin to form a 1:1 complex and behaves as a monomeric protein of an apparent molecular weight of 150 kDa.

3. Bioactivity of Wnt5a-Afamin Complex

The activity of the Wnt5a-afamin complex was evaluated based on the phosphorylation of Dvl2. The Wnt5a-afamin complex obtained by affinity purification in the above section 1 and Wnt5a purified by the conventional method (Kurayoshi et al., Biochem. J. 402, 515-523 (2007)) (with 1% (w/v) CHAPS and no tag) were separately diluted with a fresh culture medium containing 1% (w/v) BSA so that the CHAPS concentration would be 0.01% (w/v) or less.

NIH3T3 cells were cultured and then treated with each purified Wnt5a at a concentration of 0, 10, 20 or 40 ng/mL in the culture medium for 2 hours. The cells were lysed with lysis buffer (20 mM Tris-HCl [pH 8.0], 1% Nonidet P-40, 137 mM NaCl, 10% glycerol, 1 mM phenylmethylsulfonyl fluoride, 20 μg/mL aprotinin, 20 μg/mL leupeptin, 5 mM NaF, 5 mM $Na_3VO_4$ and 50 mM β-glycerophosphate), and the cell lysate was subjected to western blotting using an anti-Dvl2 antibody (Cell Signaling Technology).

Figure 15:
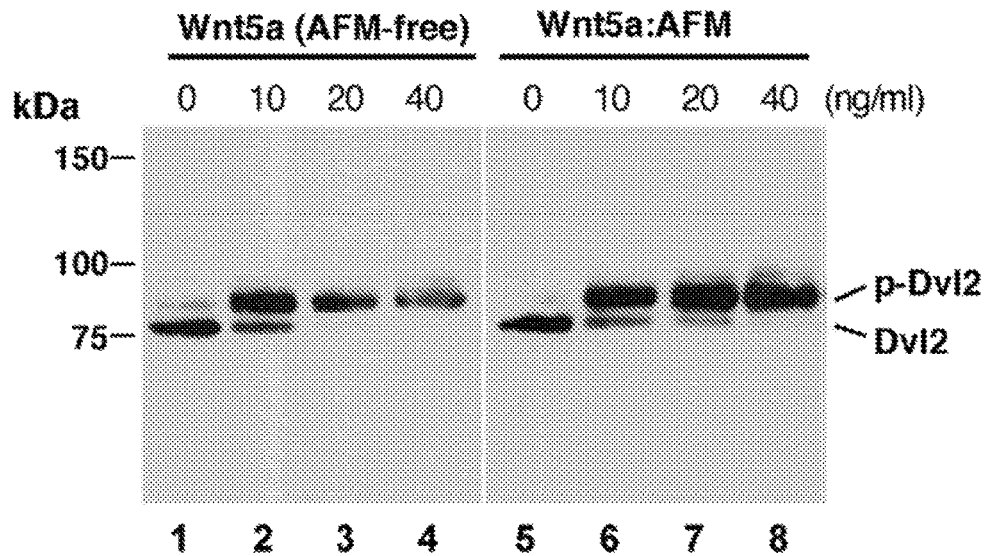
FIG. 15 shows the results of the evaluation of the activity of a Wnt5a-afamin complex or Wnt5a alone based on the phosphorylation of Dvl2.

The results are shown in FIG. 15. The left panel of FIG. 15 shows the results for the Wnt5a purified by the conventional method (not containing afamin), and the right panel of FIG. 15 shows the results for the Wnt5a-afamin complex. As shown in FIG. 15, both of these Wnt5a proteins induced the phosphorylation of Dvl2 at a concentration of 10 ng/mL or more. These results show that Wnt5a protein retains Wnt activity even after purified as a Wnt5a-afamin complex.

Example 8

Purification of Wnt Protein Using Anti-Afamin Antibody

Upon secretion from cells, Wnt protein molecules are partially captured by afamin in culture medium to form a 1:1 non-covalent complex. Thus, Wnt protein molecules are prevented from incorporation into lipoprotein particles etc., and can exist as stable molecules. However, in the presence of 1% (w/v) CHAPS, Wnt protein dissociates from the complex with afamin. Based on these properties, it was examined whether a wild-type, affinity tag-free Wnt protein could be purified from cell culture supernatant in a simple manner.

Method

To 250 mL of the culture supernatant of the cell line stably expressing tag-free Wnt3a (L-3a), 2.5 mL of a sepharose with an anti-bovine afamin monoclonal antibody (B91) immobilized thereto was added, and the mixture was rotated end over end at 4° C. for 3 hours. The mixture was loaded into an empty column to collect the sepharose, and 5 cycles of washing with 5 mL PBS were performed (wash 1 to 5). Subsequently, after addition of 2.5 mL of 1% (w/v) CHAPS/PBS, the column was allowed to stand for 10 minutes, and elution was performed in 10 cycles (elute 1 to 10). Fifteen microliters each of the collected fractions (wash 1 to 5 and elute 1 to 10) were subjected to electrophoresis under non-reducing conditions. After the electrophoresis, the gel was stained with CBB stain.

Figure 16:
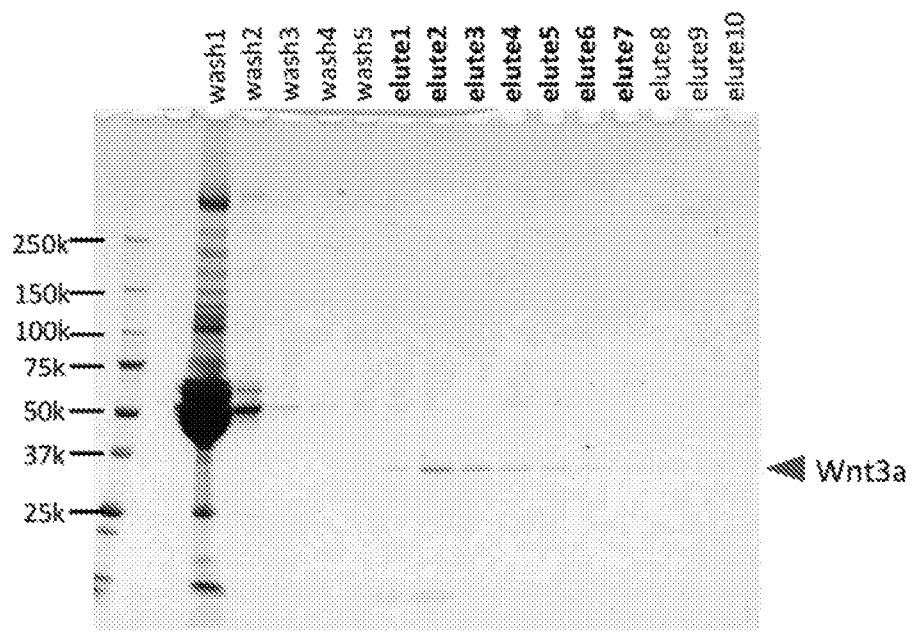
FIG. 16 shows the results of electrophoresis of wash fractions (wash 1 to 5) and elute fractions (elute 1 to 10) obtained in the course of the purification of tag-free Wnt3a from the culture supernatant of L-3a cells using an anti-bovine afamin monoclonal antibody.

The results of the electrophoresis are shown in FIG. 16. As shown in FIG. 16, when CHAPS was used as an eluent after the capture of a Wnt3a-afamin complex on the B91 column, the interaction between B91 and afamin was not disrupted by CHAPS, but Wnt3a dissociated from afamin. Thus, only Wnt3a was eluted. The eluted Wnt3a had approximately 100% purity. This method can achieve single-step purification of 6 μg of a tag-free Wnt3a protein from 250 mL of the L-3a culture supernatant using only 2.5 mL of B91-sepharose. The series of the purification procedures can be completed within one day. In contrast, the method of Non Patent Literature 7 involves as many as 4 purification steps comprising using Blue-Sepharose, HiTrap Chelating column, HiLoad 26/60 Superdex 200 and HiTrap Heparin, and further involves the steps of concentration and buffer exchange between the purification steps. Further, many days are required for purification of about 100 μg of Wnt5a from 4 L of the culture supernatant. That is, the production method of the present invention is comparable to the conventional method in terms of the yield per volume of culture supernatant, and advantageously, can provide a Wnt protein in a very simple and brief manner without use of special equipment.

Example 9

Purification of Wnt3a-Afamin Complex in Case of Co-Expression of Wnt3a and Human Afamin 1. Effect of Wnt3a/Human Afamin Co-expression on Wnt3a Secretion An N-terminally PA-tagged Wnt3a expression construct and an N-terminally TARGET-tagged human afamin expression construct were prepared. These expression constructs were transfected using Expi293 System (Life Technologies Inc.) to prepare Expi293F cells transiently co-expressing Wnt3a and human afamin. Separately, an empty vector or the PA-tagged Wnt3a expression construct was transfected using Expi293 System (Life Technologies Inc.) to prepare a different type of Expi293F cells.

The transfected cells of each type were cultured for 90 hours in a serum-free culture medium, and the supernatants were separately harvested. To 1 mL of each supernatant, 20 μL of a sepharose with the anti-PA tag antibody NZ-1 (Fujii et al., Protein Expres Purif 95, 240-247 (2014)) immobilized thereto was added, and the mixture was rotated end over end for 1 hour. The sepharose was precipitated by centrifugation, and the supernatant was removed. After the sepharose was washed 3 times with 1 mL of TBS, 30 μL of SDS sample buffer was added, and elution was performed under heating at 95° C. for 2 minutes. The eluate was subjected to electrophoresis under non-reducing conditions, and after the electrophoresis, the gel was stained with CBB stain.

Figure 17:
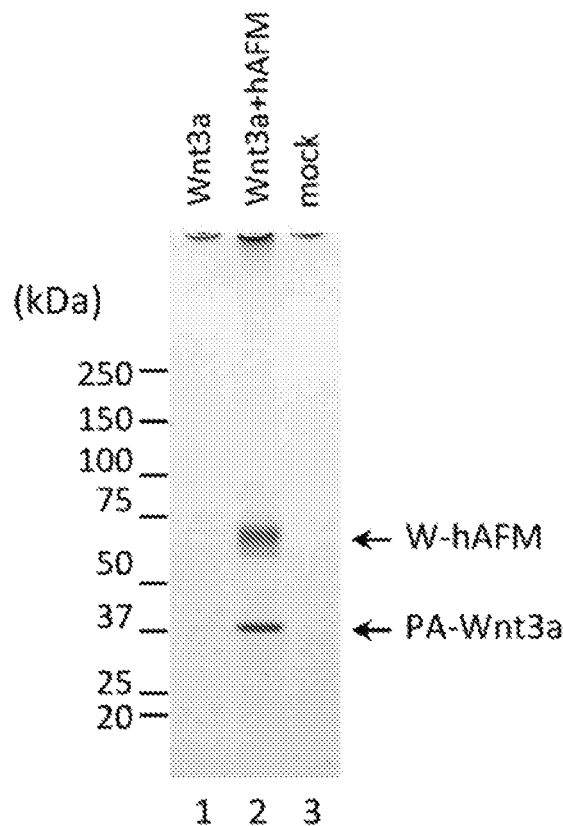
FIG. 17 shows the promoting effect of Wnt3a/human afamin co-expression on the secretion of a complex of Wnt3a and human afamin.

The results are shown in FIG. 17. Lane 3 (mock) shows the results of the immunoprecipitation using the anti-PA tag antibody NZ-1 in the culture supernatant of the cells transfected with the empty vector. Lane 1 (Wnt3a) shows the results of the immunoprecipitation using the same antibody in the culture supernatant of the cells transfected with the Wnt3a expression vector alone. Lane 2 (Wnt3a+hAFM) shows the results of the immunoprecipitation using the same antibody in the culture supernatant of the cells transfected with a mixture of the Wnt3a expression vector and the human afamin expression vector. Since this experiment used a serum-free culture medium, Wnt3a was not secreted into the culture supernatant of the cells transfected with the Wnt3a expression vector alone (lane 1). In contrast, in the culture supernatant of the Wnt3a/human afamin co-expressing cells, a Wnt3a-afamin complex was immunoprecipitated (lane 2). These results show that the co-expression of Wnt3a and afamin enables Wnt3a, which is usually not secreted at all into a serum-free culture medium, to be secreted in the form of a complex with afamin into the culture medium.

2. Purification of Wnt3a Using Anti-PA Tag Antibody

Figure 18:
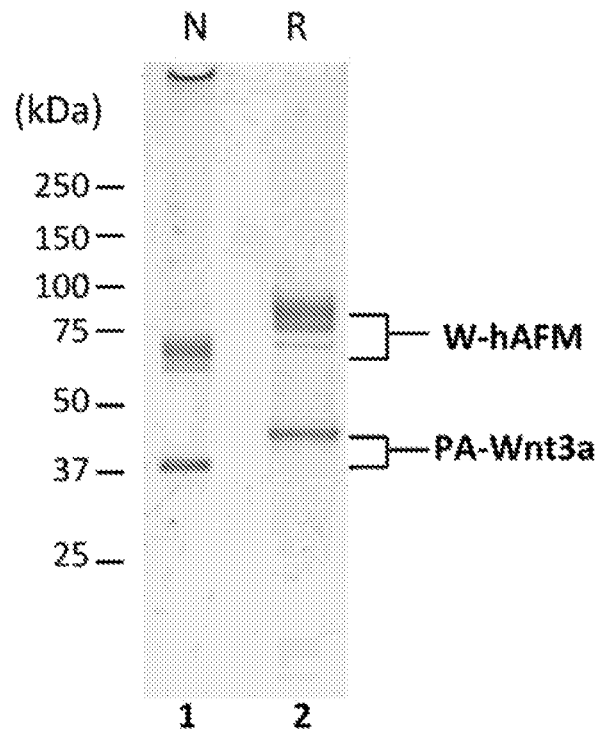
FIG. 18 shows the results of purification using an anti-PA tag antibody from the culture supernatant of Wnt3a/human afamin co-expressing cells.

In the same manner as described above, the Expi293F cells transiently co-expressing a PA-tagged Wnt3a and a TARGET-tagged human afamin were cultured for 90 hours, the culture supernatant was harvested, and a 1/100 amount of NZ-1-sepharose was added to the culture supernatant to allow the resin to capture a Wnt3a/human afamin complex. After the resin was washed with TBS, elution was performed with TBS containing 0.1 mg/mL PA14 peptide (EGGVAMP-GAEDDVV, SEQ ID NO: 11) to give a purified PA-tagged Wnt3a. As is clear from FIG. 18, the results of lane 1 (NR: non-reducing conditions) and lane 2 (R: reducing conditions) show that the eluate obviously contained Wnt3a and human afamin but hardly contained impurities. That is, it was shown that the Wnt3a-afamin complex can be purified in a single step using the anti-PA tag antibody NZ-1 from the culture supernatant of the cells co-expressing Wnt3a and human afamin. Although data are not shown, the yield of Wnt3a by the above-mentioned method was about 170 µg from 300 mL of the culture supernatant of the Wnt3a/human afamin co-expressing cells. This yield is more than 20-fold higher than that of the conventional purification method (Non Patent Literature 7).

Figure 19:
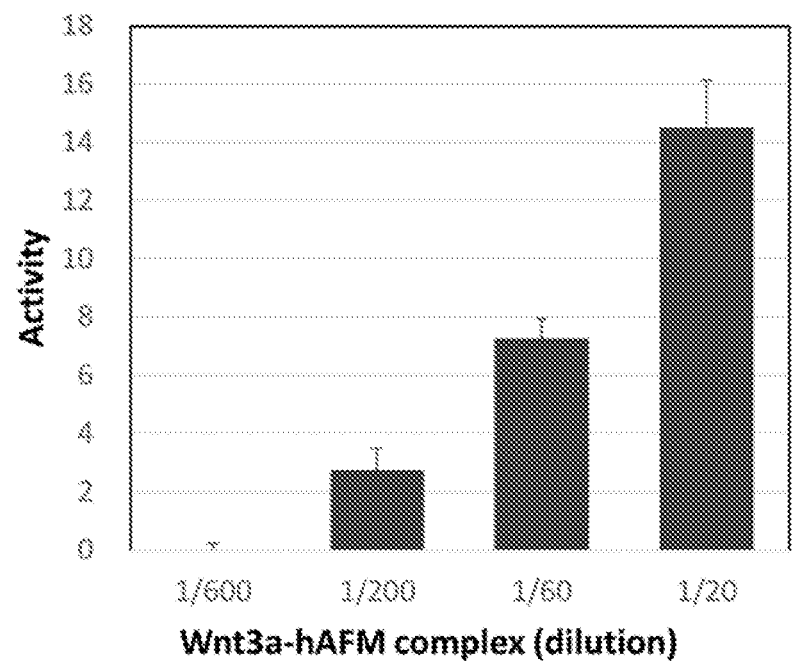
FIG. 19 shows the results of TCF reporter assay to confirm the activity of a complex purified from the culture supernatant of Wnt3a/human afamin co-expressing cells.

The (PA-tagged) Wnt3a-(TARGET-tagged) afamin complex purified from the culture supernatant of the Wnt3a/human afamin co-expressing cells as described above was diluted in the same manner as in Example 5 and then subjected to TCF reporter assay. As shown in FIG. 19, the activity was observed at 100 ng/mL (1/200 dilution) or higher concentrations, and judging from the concentration dependency, the Wnt activity was comparable to that of the Wnt3a-afamin complex purified from a serum-containing culture medium (FIG. 12).

3. Gel Filtration Chromatography of Wnt3a-Afamin Complex

The complex purified from the culture supernatant of the Wnt3a/human afamin co-expressing cells was subjected to gel filtration chromatography. AKTA FPLC chromatography system (GE Healthcare) was used for gel filtration. The column used was Superdex 200 10/300 GL, and the buffer used was PBS. The flow rate was set to 0.5 mL/min. The fractions of two peaks that appeared in the chromatogram and the sample before use in the gel filtration chromatography were subjected to SDS gel electrophoresis and Coomassie staining.

Figure 20:
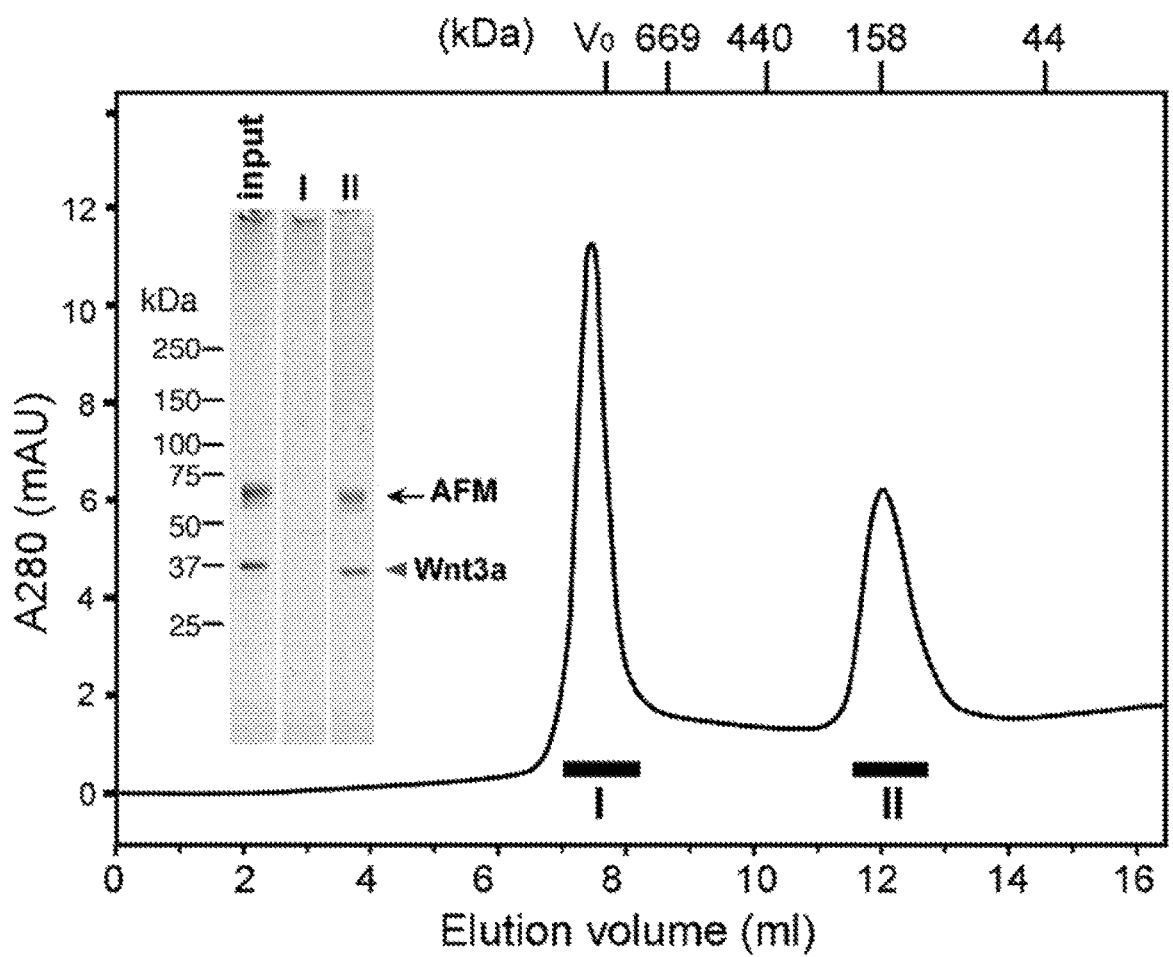
FIG. 20 shows the gel filtration chromatogram of a complex obtained by Wnt3a/human afamin co-expression and also shows the results of SDS-PAGE of the fractions of the two peaks in the gel filtration chromatogram.

The results are shown in FIG. 20. As is clear from the chromatography chart, two peaks appeared, one in the void volume (Vo) corresponding to the high-molecular-weight region and the other at about 150 kDa. As is clear from the electrophoretic results, fraction I contained high molecular aggregates, and fraction II contained afamin and Wnt3a in equal amounts. "Input" means the sample before use in the gel filtration.

Example 10

Wnt Secretion upon Co-expression of Various Types of Human Wnt Proteins and Human Afamin For 12 human Wnt proteins (Wnt1, Wnt2b, Wnt3, Wnt3a, Wnt5a, Wnt7a, Wnt7b, Wnt8a, Wnt9a, Wnt9b, Wnt10a and Wnt10b), N-terminally PA-tagged human Wnt expression constructs were prepared. In the same manner as in Example 9, these human Wnt expression constructs were separately transfected in combination with an N-terminally TARGET-tagged human afamin expression construct using Expi293 System (Life Technologies Inc.) to prepare 12 types of Expi293F cells transiently co-expressing human Wnt and human afamin. Separately, the 12 types of PA-tagged human Wnt expression constructs alone were separately transfected using Expi293 System (Life Technologies Inc.) to prepare different types of Expi293F cells.

The transfected cells of each type were cultured for 90 hours in a serum-free culture medium, and the supernatants were separately harvested. To 1 mL of each supernatant, 20 µL of NZ-1-sepharose or P20.1-sepharose was added, and the mixture was rotated end over end for 1 hour. The sepharose was precipitated by centrifugation, and the supernatant was removed. After the sepharose was washed 3 times with 1 mL of TBS, 30 µL of SDS sample buffer was added, and elution was performed under heating at 95° C. for 2 minutes. The eluate was subjected to western blotting using biotin-modified NZ-1.

Figure 21:
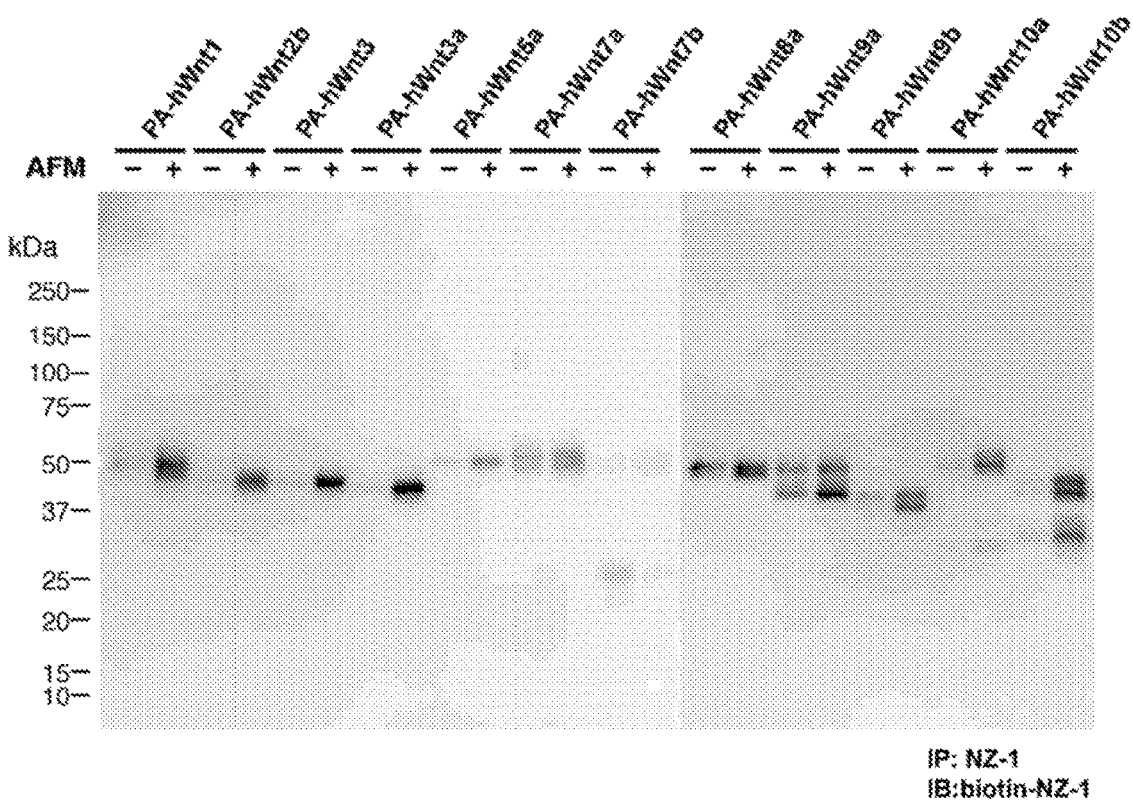
FIG. 21 shows the results of western blotting using a biotin-modified anti-PA tag antibody to analyze the immunoprecipitates obtained using an anti-PA tag antibody from the culture supernatants of 12 different types of human Wnt/human afamin co-expressing cells, each type of which expresses a different type of human Wnt.
Figure 22:
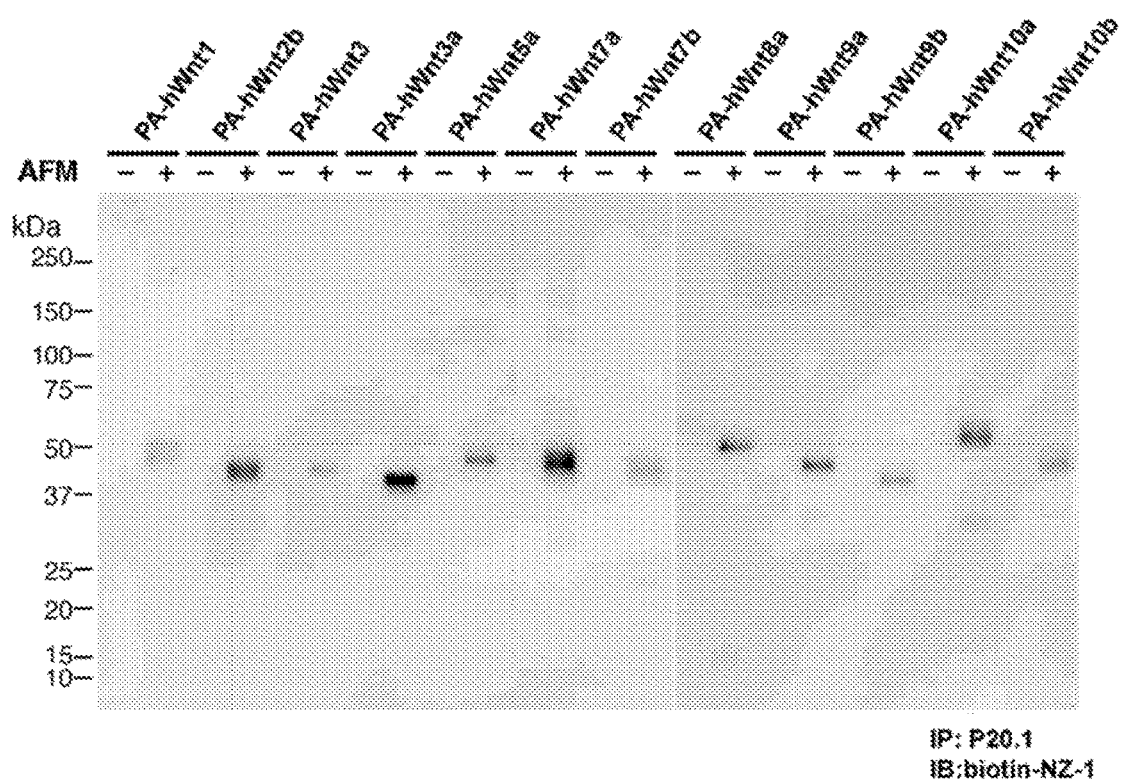
FIG. 22 shows the results of western blotting using a biotin-modified anti-PA tag antibody to analyze the immunoprecipitates obtained using P20.1 antibody from the culture supernatant is of 12 different types of human Wnt/human afamin co-expressing cells, each type of which expresses a different type of human Wnt.

FIG. 21 shows the results of the samples subjected to immunoprecipitation using NZ-1-sepharose, and FIG. 22 shows the results of the samples subjected to immunoprecipitation using P20.1-sepharose. As is clear from FIG. 21, all the 12 human Wnt proteins were secreted at higher levels in the culture supernatants of the Wnt-afamin co-expressing cells (AFM+) than those in the culture supernatants of the Wnt expressing cells (AFM−). As is clear from FIG. 22, all the types of Wnt proteins were detected in the culture supernatants of the Wnt-afamin co-expressing cells (AFM+) by immunoprecipitation using an antibody for the TARGET tag, which was fused with afamin. This result shows that all the 12 human Wnt proteins form a complex with afamin.

Example 11

Gel Filtration Chromatography of Human Wnt3-Human Afamin Complex

A complex purified from the culture supernatant of the human Wnt3/human afamin co-expressing cells was subjected to gel filtration chromatography. AKTA FPLC chromatography system (GE Healthcare) was used for gel filtration. The column used was Superdex 200 10/300 GL, and the buffer used was PBS. The flow rate was set to 0.5 mL/min. The fractions of two peaks that appeared in the chromatogram and the sample before use in the gel filtration chromatography were subjected to SDS gel electrophoresis and Coomassie staining.

Figure 23:
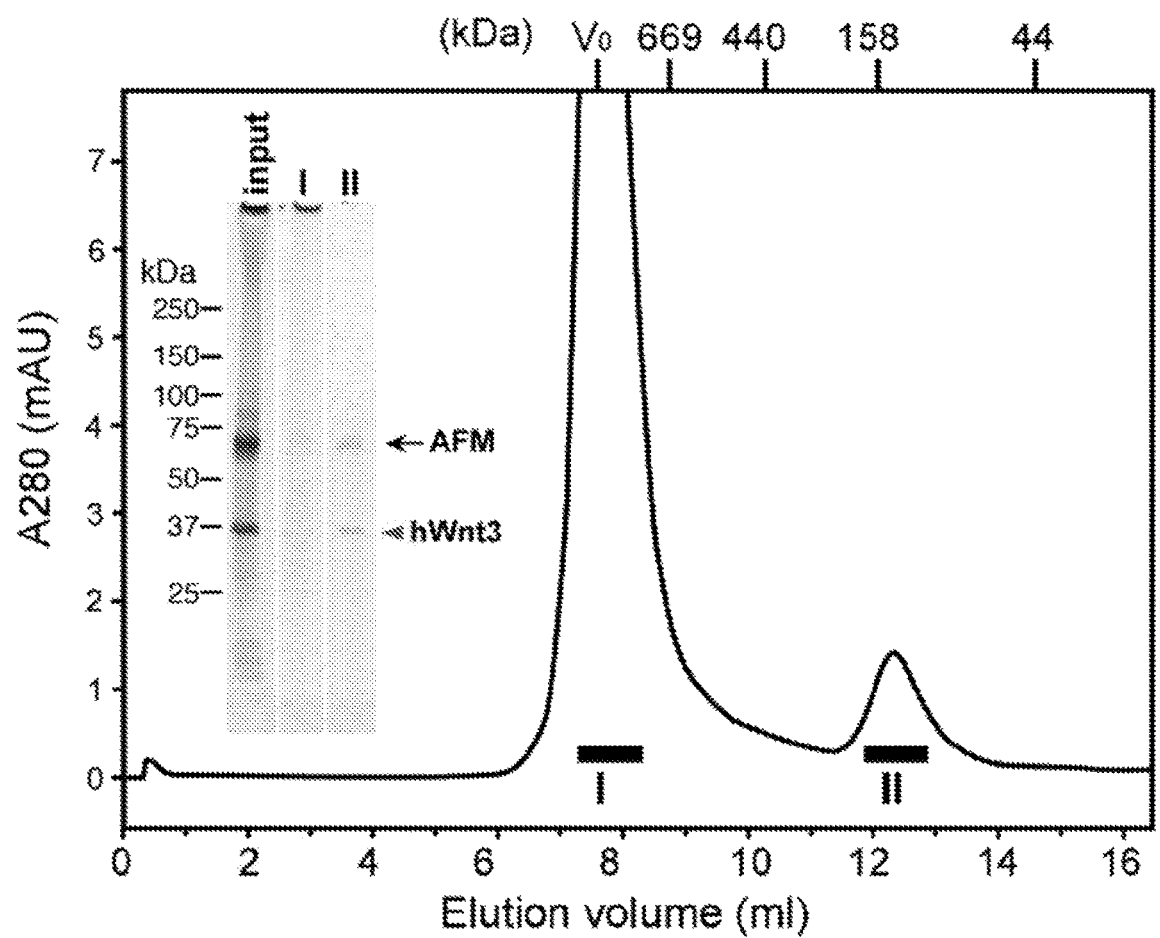
FIG. 23 shows the gel filtration chromatogram of a complex obtained by human Wnt3/human afamin co-expression and also shows the results of SDS-PAGE of the fractions of the two peaks in the gel filtration chromatogram.

The results are shown in FIG. 23. As is clear from the chromatography chart, two peaks appeared, one in the void volume (Vo) corresponding to the high-molecular-weight region and the other at about 150 kDa. As is clear from the electrophoretic results, fraction I contained high molecular aggregates, and fraction II contained afamin and Wnt3 in equal amounts. "Input" means the sample before use in the gel filtration.

The present invention is not limited to the particular embodiments and examples described above, and various modifications can be made within the scope of the appended claims. Other embodiments provided by suitably combining technical means disclosed in separate embodiments of the present invention are also within the technical scope of the present invention. All the academic publications and patent literature cited in the description are incorporated herein by reference.

The invention claimed is:

1. A method for producing a Wnt protein from a culture product, the method comprising culturing Wnt protein-expressing cells in an afamin-containing culture medium to obtain the culture product, the method further comprising
   (1) a step of performing affinity purification targeting afamin to obtain a Wnt protein from the culture product, and/or
   (2) a step of performing affinity purification to obtain a Wnt protein in the form of a complex with afamin from the culture product,
   wherein the complex is formed by Wnt protein and afamin derived from an organism different from Wnt protein, or the complex contains Wnt protein having an affinity tag and/or afamin having an affinity tag.

2. The method according to claim 1, wherein the culture product contains no surfactants.

3. The method according to claim 1, wherein the method uses no surfactants.

4. The method according to claim 1, wherein the Wnt protein produced is in the form of a complex with afamin and has Wnt activity.

5. The method according to claim 1, wherein the afamin-containing culture medium is a serum-containing culture medium.

6. The method according to claim 5, wherein the serum is bovine serum.

7. The method according to claim 1, wherein the afamin-containing culture medium is a culture medium supplemented with purified afamin.

8. The method according to claim 7, wherein the purified afamin is a recombinant afamin having an affinity tag.

9. The method according to claim 1, wherein the afamin-containing culture medium is a culture medium containing afamin secreted from afamin-expressing cells cultured therein.

10. The method according to claim 9, wherein the afamin-expressing cells are cells expressing both the Wnt protein and afamin.

11. The method according to claim 9, wherein the afamin secreted from the afamin-expressing cells is a recombinant afamin having an affinity tag.

12. The method according to claim 1, wherein the Wnt protein is selected from the group consisting of Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11 and Wnt16.

13. A method for storing a Wnt protein having Wnt activity in a surfactant-free solution, the method comprising storing a purified Wnt protein in the form of a complex with afamin produced by the method of claim 1 in a surfactant-free solution, wherein the complex is formed by Wnt protein and afamin derived from an organism different from Wnt protein, or the complex contains Wnt protein having an affinity tag and/or afamin having an affinity tag.

14. A purified Wnt protein-afamin complex having Wnt activity,
wherein the complex is formed by Wnt protein and afamin derived from an organism different from Wnt protein, or the complex contains Wnt protein having an affinity tag and/or afamin having an affinity tag.

15. A Wnt signaling activator containing a purified Wnt protein-afamin complex, wherein the complex is formed by Wnt protein and afamin derived from an organism different from Wnt protein, or the complex contains Wnt protein having an affinity tag and/or afamin having an affinity tag.

* * * * *

SEQUENCE LISTING

<160> NUMBER OF SEQ ID NOS: 11

<210> SEQ ID NO 1
<211> LENGTH: 4
<212> TYPE: PRT
<213> ORGANISM: Artificial
<220> FEATURE:
<223> OTHER INFORMATION: Tag sequence

<400> SEQUENCE: 1

Tyr Pro Gly Gln
1

<210> SEQ ID NO 2
<211> LENGTH: 12
<212> TYPE: PRT
<213> ORGANISM: Artificial
<220> FEATURE:
<223> OTHER INFORMATION: Tag sequence

<400> SEQUENCE: 2

Gly Val Ala Met Pro Gly Ala Glu Asp Asp Val Val
1               5                   10

<210> SEQ ID NO 3
<211> LENGTH: 8
<212> TYPE: PRT
<213> ORGANISM: Artificial
<220> FEATURE:
<223> OTHER INFORMATION: PAR4-C8 peptide

<400> SEQUENCE: 3

Pro Arg Gly Tyr Pro Gly Gln Val
1               5

<210> SEQ ID NO 4
<211> LENGTH: 334
<212> TYPE: PRT
<213> ORGANISM: Mus musculus

<400> SEQUENCE: 4

Ser Tyr Pro Ile Trp Trp Ser Leu Ala Val Gly Pro Gln Tyr Ser Ser
1               5                   10                  15

Leu Ser Thr Gln Pro Ile Leu Cys Ala Ser Ile Pro Gly Leu Val Pro
                20                  25                  30

Lys Gln Leu Arg Phe Cys Arg Asn Tyr Val Glu Ile Met Pro Ser Val
            35                  40                  45

Ala Glu Gly Val Lys Ala Gly Ile Gln Glu Cys Gln His Gln Phe Arg
        50                  55                  60

Gly Arg Arg Trp Asn Cys Thr Thr Val Ser Asn Ser Leu Ala Ile Phe
65                  70                  75                  80

Gly Pro Val Leu Asp Lys Ala Thr Arg Glu Ser Ala Phe Val His Ala
                85                  90                  95

Ile Ala Ser Ala Gly Val Ala Phe Ala Val Thr Arg Ser Cys Ala Glu
            100                 105                 110

Gly Ser Ala Ala Ile Cys Gly Cys Ser Ser Arg Leu Gln Gly Ser Pro
        115                 120                 125

Gly Glu Gly Trp Lys Trp Gly Gly Cys Ser Glu Asp Ile Glu Phe Gly
    130                 135                 140

Gly Met Val Ser Arg Glu Phe Ala Asp Ala Arg Glu Asn Arg Pro Asp
145                 150                 155                 160

```
Ala Arg Ser Ala Met Asn Arg His Asn Asn Glu Ala Gly Arg Gln Ala
            165                 170                 175

Ile Ala Ser His Met His Leu Lys Cys Lys Cys His Gly Leu Ser Gly
        180                 185                 190

Ser Cys Glu Val Lys Thr Cys Trp Trp Ser Gln Pro Asp Phe Arg Thr
        195                 200                 205

Ile Gly Asp Phe Leu Lys Asp Lys Tyr Asp Ser Ala Ser Glu Met Val
        210                 215                 220

Val Glu Lys His Arg Glu Ser Arg Gly Trp Val Glu Thr Leu Arg Pro
225                 230                 235                 240

Arg Tyr Thr Tyr Phe Lys Val Pro Thr Glu Arg Asp Leu Val Tyr Tyr
                245                 250                 255

Glu Ala Ser Pro Asn Phe Cys Glu Pro Asn Pro Glu Thr Gly Ser Phe
            260                 265                 270

Gly Thr Arg Asp Arg Thr Cys Asn Val Ser Ser His Gly Ile Asp Gly
        275                 280                 285

Cys Asp Leu Leu Cys Cys Gly Arg Gly His Asn Ala Arg Thr Glu Arg
290                 295                 300

Arg Arg Glu Lys Cys His Cys Val Phe His Trp Cys Cys Tyr Val Ser
305                 310                 315                 320

Cys Gln Glu Cys Thr Arg Val Tyr Asp Val His Thr Cys Lys
                325                 330

<210> SEQ ID NO 5
<211> LENGTH: 63
<212> TYPE: PRT
<213> ORGANISM: Artificial
<220> FEATURE:
<223> OTHER INFORMATION: Tag sequence

<400> SEQUENCE: 5

Met Leu Asp Ala Ser Gly Cys Ser Trp Ala Met Trp Thr Trp Ala Leu
1               5                   10                  15

Leu Gln Leu Leu Leu Leu Val Gly Pro Gly Gly Cys Gly Arg Gly Tyr
            20                  25                  30

Pro Gly Gln Tyr Pro Gly Gln Tyr Pro Gly Gln Tyr Pro Gly Gln Tyr
        35                  40                  45

Pro Gly Gln Val Arg Glu Asn Leu Tyr Phe Gln Gly Lys Asp Gly
    50                  55                  60

<210> SEQ ID NO 6
<211> LENGTH: 28
<212> TYPE: PRT
<213> ORGANISM: Artificial
<220> FEATURE:
<223> OTHER INFORMATION: signal sequence

<400> SEQUENCE: 6

Met Leu Asp Ala Ser Gly Cys Ser Trp Ala Met Trp Thr Trp Ala Leu
1               5                   10                  15

Leu Gln Leu Leu Leu Leu Val Gly Pro Gly Gly Cys
            20                  25

<210> SEQ ID NO 7
<211> LENGTH: 21
<212> TYPE: PRT
<213> ORGANISM: Artificial
<220> FEATURE:
<223> OTHER INFORMATION: Tag sequence
```

```
<400> SEQUENCE: 7

Tyr Pro Gly Gln Tyr Pro Gly Gln Tyr Pro Gly Gln Tyr Pro Gly Gln
1               5                   10                  15

Tyr Pro Gly Gln Val
            20

<210> SEQ ID NO 8
<211> LENGTH: 11
<212> TYPE: PRT
<213> ORGANISM: Artificial
<220> FEATURE:
<223> OTHER INFORMATION: eTEV sequence

<400> SEQUENCE: 8

Arg Glu Asn Leu Tyr Phe Gln Gly Lys Asp Gly
1               5                   10

<210> SEQ ID NO 9
<211> LENGTH: 10
<212> TYPE: PRT
<213> ORGANISM: Artificial
<220> FEATURE:
<223> OTHER INFORMATION: Tag sequence

<400> SEQUENCE: 9

Gly Arg Gly Tyr Pro Gly Gln Tyr Pro Gly
1               5                   10

<210> SEQ ID NO 10
<211> LENGTH: 10
<212> TYPE: PRT
<213> ORGANISM: Bos taurus

<400> SEQUENCE: 10

Leu Pro Thr Gln Pro Gln Asp Val Asp Asp
1               5                   10

<210> SEQ ID NO 11
<211> LENGTH: 14
<212> TYPE: PRT
<213> ORGANISM: Artificial
<220> FEATURE:
<223> OTHER INFORMATION: PA14 peptide

<400> SEQUENCE: 11

Glu Gly Gly Val Ala Met Pro Gly Ala Glu Asp Asp Val Val
1               5                   10
```